(12) United States Patent
Moskowitz et al.

(10) Patent No.: US 10,952,723 B2
(45) Date of Patent: *Mar. 23, 2021

(54) ARTIFICIAL INTERVERTEBRAL IMPANT

(71) Applicant: Moskowitz Family LLC, Rockville, MD (US)

(72) Inventors: Mosheh T. Moskowitz, Rockville, MD (US); Nathan C. Moskowitz, Rockville, MD (US)

(73) Assignee: Moskowitz Family LLC, Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/362,152

(22) Filed: Mar. 22, 2019

(65) Prior Publication Data

US 2019/0282230 A1 Sep. 19, 2019

Related U.S. Application Data

(60) Continuation of application No. 15/934,622, filed on Mar. 23, 2018, now Pat. No. 10,251,643, which is a
(Continued)

(51) Int. Cl.
  *A61B 17/064* (2006.01)
  *A61B 17/068* (2006.01)
  (Continued)

(52) U.S. Cl.
  CPC ...... *A61B 17/0642* (2013.01); *A61B 17/0643* (2013.01); *A61B 17/0682* (2013.01);
  (Continued)

(58) Field of Classification Search
  CPC ............ A61B 17/0642; A61B 17/0643; A61B 17/0682; A61B 17/7064;
  (Continued)

(56) References Cited

U.S. PATENT DOCUMENTS 4,554,914 A * 11/1985 Kapp ..................... A61F 2/441
  606/86 A
4,599,086 A * 7/1986 Doty ........................ A61F 2/44
  606/86 A (Continued)

FOREIGN PATENT DOCUMENTS

FR 2727003 5/1996
WO WO 2004052245 6/2004
(Continued)

OTHER PUBLICATIONS

E.K. Wai et al., "Disk Replacement Arthroplasties: Can The Success of Hip and Knee Replacements be Repeated in the Spine?," Seminars in Spine Surgery, vol. 15, No. 4 (Dec. 2003), pp. 473-482.
(Continued)

*Primary Examiner* — Pedro Philogene
(74) *Attorney, Agent, or Firm* — Fish & Richardson P.C.

(57) ABSTRACT

An apparatus and method for joining members together using a self-drilling screw apparatus or stapling apparatus are disclosed. The screw apparatus includes a shell and first and second first screw members having tapered ends and threaded bodies that are disposed within the shell. A drive mechanism rotatably drives the first and second screw members from the shell in opposite directions and causes the screw members to embed themselves in the members to be joined. The screw apparatus can be used to join members such as bones, portions of the spinal column, vertebral bodies, wood, building materials, metals, masonry, or plastics. The stapling apparatus includes first and second lever arms rotatably joined together at a fulcrum, and the lever arms rotate in opposite directions. First and second cartridges are disposed at the ends of the lever arms. Each cartridge is capable of holding a staple including a bracket, a nail member and an alignment slot. When the ends of the lever arms are rotated towards each other the staples from
(Continued)

the cartridges are interlocked. The staples can be also be used to join members such as bones, portions of the spinal column, or vertebral bodies.

38 Claims, 25 Drawing Sheets

Related U.S. Application Data continuation of application No. 13/093,812, filed on Apr. 25, 2011, now Pat. No. 9,924,940, which is a continuation of application No. 12/347,990, filed on Dec. 31, 2008, now Pat. No. 7,951,180, which is a division of application No. 11/208,644, filed on Aug. 23, 2005, now Pat. No. 7,704,279.

(60) Provisional application No. 60/670,231, filed on Apr. 12, 2005.

(51) Int. Cl.
    *A61B 17/70*     (2006.01)
    *A61F 2/44*     (2006.01)
    *A61F 2/28*     (2006.01)
    *A61F 2/30*     (2006.01)

(52) U.S. Cl.
    CPC ........ *A61B 17/7064* (2013.01); *A61F 2/4455* (2013.01); *A61B 2017/0648* (2013.01); *A61F 2002/2835* (2013.01); *A61F 2002/3052* (2013.01); *A61F 2002/3085* (2013.01); *A61F 2002/30525* (2013.01); *A61F 2002/30579* (2013.01); *A61F 2002/30841* (2013.01); *A61F 2002/448* (2013.01); *A61F 2220/0025* (2013.01); *A61F 2310/00796* (2013.01)

(58) Field of Classification Search
    CPC ........... A61B 2017/0648; A61F 2/4455; A61F 2/442; A61F 2/30744; A61F 2/28; A61F 2002/2835; A61F 2002/3052; A61F 2002/30525; A61F 2002/30579; A61F 2002/30841; A61F 2002/3038; A61F 2002/448; A61F 2002/30556; A61F 2002/30593; A61F 2002/30774; A61F 2002/30784; A61F 2002/30062; A61F 2002/30131; A61F 2002/30515; A61F 2220/0025; A61F 2230/0013; A61F 2230/0097; A61F 2210/0004; A61F 2250/0009; A61F 2250/001; A61F 2310/00796; A61F 2310/00023; A61F 2310/00131; A61F 2310/00359; A61F 2310/0017; A61F 2002/30518; A61F 2002/30566; A61F 2002/30545; A61F 2002/20571; A61F 2002/30777; A61F 2002/2817; A61F 2002/30523; A61F 2002/30785; A61F 2002/30306
    USPC .... 623/17.11–17.16; 606/246–279, 300–328
See application file for complete search history.

(56) References Cited

U.S. PATENT DOCUMENTS

| | | | |
|---|---|---|---|
| 4,636,217 A * | 1/1987 | Ogilvie .................... | A61F 2/44 606/247 |
| 4,960,420 A | 10/1990 | Goble et al. | |
| 4,994,063 A | 2/1991 | Gamer | |
| 4,997,432 A | 3/1991 | Keller | |
| 5,062,850 A * | 11/1991 | MacMillan ............... | A61F 2/44 623/17.11 |
| 5,123,926 A | 6/1992 | Pisharodi | |
| 5,236,460 A * | 8/1993 | Barber ................... | A61F 2/4611 623/17.15 |
| 5,290,312 A | 3/1994 | Kojimoto et al. | |
| 5,458,641 A | 10/1995 | Ramirez Jimenez | |
| 5,514,180 A | 5/1996 | Heggeness et al. | |
| 5,572,653 A | 11/1996 | DeTemple et al. | |
| 5,660,188 A | 8/1997 | Groiso | |
| 5,667,472 A | 9/1997 | Finn et al. | |
| 5,669,912 A | 9/1997 | Spetzler | |
| 5,702,455 A | 12/1997 | Saggar | |
| 5,722,976 A | 3/1998 | Brown | |
| 5,782,832 A | 7/1998 | Larsen et al. | |
| 5,800,547 A * | 9/1998 | Schafer ................... | A61F 2/442 623/17.16 |
| 5,960,522 A | 10/1999 | Boe | |
| 6,106,556 A | 8/2000 | Demopulos et al. | |
| 6,113,638 A | 9/2000 | Williams et al. | |
| 6,126,689 A | 10/2000 | Brett | |
| 6,224,602 B1 | 5/2001 | Hayes | |
| 6,235,034 B1 | 5/2001 | Bray | |
| 6,322,562 B1 | 11/2001 | Wolter | |
| 6,342,074 B1 | 1/2002 | Simpson | |
| 6,368,350 B1 | 4/2002 | Erickson et al. | |
| 6,375,682 B1 | 4/2002 | Fleischmann et al. | |
| 6,419,704 B1 | 7/2002 | Ferree | |
| 6,432,106 B1 * | 8/2002 | Fraser .................. | A61F 2/30771 623/17.11 |
| 6,454,806 B1 | 9/2002 | Cohen et al. | |
| 6,454,807 B1 | 9/2002 | Jackson | |
| 6,458,159 B1 | 10/2002 | Thalgott | |
| 6,527,803 B1 | 3/2003 | Crozet et al. | |
| 6,527,804 B1 | 3/2003 | Gauchet et al. | |
| 6,533,818 B1 | 3/2003 | Weber et al. | |
| 6,572,653 B1 | 6/2003 | Simonson | |
| 6,579,318 B2 | 6/2003 | Varga et al. | |
| 6,582,468 B1 | 6/2003 | Gauchet | |
| 6,629,998 B1 | 10/2003 | Lin | |
| 6,641,614 B1 | 11/2003 | Wagner et al. | |
| 6,716,247 B2 | 4/2004 | Michelson | |
| 6,719,794 B2 | 4/2004 | Gerber | |
| 6,723,126 B1 * | 4/2004 | Berry .................... | A61F 2/4611 623/17.11 |
| 6,730,088 B2 | 5/2004 | Yeh | |
| 6,733,532 B1 | 5/2004 | Gauchet et al. | |
| 6,752,832 B2 | 6/2004 | Neumann | |
| 6,764,491 B2 | 7/2004 | Frey et al. | |
| 6,770,094 B2 | 8/2004 | Fehling et al. | |
| 6,890,355 B2 | 5/2005 | Michelson | |
| 6,904,308 B2 | 6/2005 | Frisch et al. | |
| 6,953,477 B2 | 10/2005 | Berry | |
| 6,955,671 B2 | 10/2005 | Uchikubo | |
| 7,028,878 B2 | 4/2006 | Bauer | |
| 7,030,904 B2 | 4/2006 | Adair et al. | |
| 7,037,258 B2 | 5/2006 | Chatenever et al. | |
| 7,097,615 B2 | 8/2006 | Banik et al. | |
| 7,211,112 B2 | 5/2007 | Baynham et al. | |
| 7,226,480 B2 * | 6/2007 | Thalgott ............... | A61F 2/4465 623/17.11 |
| 7,232,464 B2 | 6/2007 | Mathieu et al. | |
| 7,238,203 B2 | 7/2007 | Bagga et al. | |
| 7,442,209 B2 | 10/2008 | Michelson | |
| 7,641,693 B2 | 1/2010 | Gutlin et al. | |
| 7,674,296 B2 | 3/2010 | Rhoda et al. | |
| 7,691,147 B2 * | 4/2010 | Gutlin ..................... | A61F 2/44 623/17.15 |
| 7,704,279 B2 | 4/2010 | Moskowitz et al. | |
| 7,753,958 B2 | 7/2010 | Gordon et al. | |
| 7,776,047 B2 | 8/2010 | Fanger et al. | |
| 8,268,000 B2 | 9/2012 | Waugh et al. | |
| 9,924,940 B2 * | 3/2018 | Moskowitz ........ | A61B 17/0642 |
| 10,238,383 B2 * | 3/2019 | Moskowitz ........ | A61B 17/0642 |
| 10,251,643 B2 * | 4/2019 | Moskowitz ........ | A61B 17/0642 |
| 2002/0068977 A1 | 6/2002 | Jackson | |
| 2002/0143338 A1 | 10/2002 | Othay et al. | |
| 2002/0143399 A1 | 10/2002 | Sutcliffe | |
| 2004/0088054 A1 | 5/2004 | Berry | |
| 2004/0177531 A1 | 9/2004 | DiBenedetto et al. | |
| 2004/0186569 A1 | 9/2004 | Berry | |

(56) References Cited

U.S. PATENT DOCUMENTS

| | | |
|---|---|---|
| 2004/0254644 A1 | 12/2004 | Taylor |
| 2005/0027362 A1 | 2/2005 | Williams et al. |
| 2005/0049590 A1* | 3/2005 | Alleyne ................. A61F 2/442 623/17.11 |
| 2005/0177235 A1 | 8/2005 | Baynham et al. |
| 2005/0177236 A1 | 8/2005 | Mathieu et al. |
| 2005/0216084 A1 | 9/2005 | Fleischmann |
| 2005/0256576 A1 | 11/2005 | Moskowitz et al. |
| 2005/0261769 A1 | 11/2005 | Moskowitz et al. |
| 2005/0273170 A1 | 12/2005 | Navarro et al. |
| 2005/0278026 A1 | 12/2005 | Gordon et al. |
| 2006/0241621 A1 | 10/2006 | Moskowitz et al. |
| 2007/0049943 A1 | 3/2007 | Moskowitz et al. |
| 2007/0167678 A1 | 7/2007 | Moskowitz et al. |
| 2007/0198089 A1 | 8/2007 | Moskowitz et al. |
| 2007/0213820 A1 | 9/2007 | Magerl et al. |
| 2007/0250172 A1 | 10/2007 | Moskowitz et al. |
| 2008/0033440 A1 | 2/2008 | Moskowitz et al. |
| 2008/0177307 A1 | 7/2008 | Moskowitz et al. |
| 2008/0281424 A1 | 11/2008 | Parry et al. |
| 2009/0105831 A1 | 4/2009 | Jones et al. |
| 2009/0112271 A1 | 4/2009 | Moskowitz et al. |
| 2009/0224023 A1 | 9/2009 | Moskowitz et al. |
| 2009/0234455 A1 | 9/2009 | Moskowitz et al. |
| 2010/0145460 A1 | 6/2010 | McDonough et al. |
| 2010/0324606 A1 | 12/2010 | Moskowitz et al. |
| 2011/0125269 A1 | 5/2011 | Moskowitz et al. |
| 2011/0137349 A1 | 6/2011 | Moskowitz et al. |
| 2011/0178600 A1 | 7/2011 | Moskowitz et al. |
| 2011/0208312 A1 | 8/2011 | Moskowitz et al. |
| 2011/0288646 A1 | 11/2011 | Moskowitz et al. |
| 2011/0295327 A1 | 12/2011 | Moskowitz et al. |
| 2011/0295371 A1 | 12/2011 | Moskowitz et al. |
| 2011/0307011 A1 | 12/2011 | Moskowitz et al. |
| 2011/0319935 A1 | 12/2011 | Moskowitz et al. |
| 2012/0010714 A1 | 1/2012 | Moskowitz et al. |
| 2012/0330419 A1 | 12/2012 | Moskowitz et al. |
| 2013/0018468 A1 | 1/2013 | Moskowitz et al. |
| 2013/0018469 A1 | 1/2013 | Moskowitz et al. |
| 2013/0018470 A1 | 1/2013 | Moskowitz et al. |
| 2013/0023992 A1 | 1/2013 | Moskowitz et al. |
| 2013/0053962 A1 | 2/2013 | Moskowitz et al. |
| 2013/0173002 A1 | 7/2013 | Moskowitz et al. |
| 2013/0282017 A1 | 10/2013 | Moskowitz et al. |
| 2014/0249629 A1 | 9/2014 | Moskowitz et al. |
| 2015/0025637 A1 | 1/2015 | Moskowitz et al. |
| 2015/0105824 A1 | 4/2015 | Moskowitz et al. |
| 2015/0148847 A1 | 5/2015 | Moskowitz et al. |
| 2016/0374830 A1 | 12/2016 | Moskowitz et al. |
| 2017/0252178 A1 | 9/2017 | Moskowitz et al. |

FOREIGN PATENT DOCUMENTS

| | | |
|---|---|---|
| WO | WO 2004/093749 | 11/2004 |
| WO | WO 2006/091503 | 8/2006 |

OTHER PUBLICATIONS

International Search Report (ISR and Written Opinion of the International Searching Authority, dated May 21, 2008, International Application No. PC /US2007/021015.

International Search Report (ISR and Written Opinion of the International Searching Authority, dated Jul. 9, 2008, International Application No. PC /US2007/021013.

International Search Report (ISR) and Written Opinion of the International Searching Authority, dated Dec. 3, 2007, International Application No. PCT/US 07/05005.

Richard D. Guyer et al., "Intervertebral Disc Prostheses," Spine Journal, vol. 28, No. 15S, Supp. To Aug. 1, 2003, pp. S15-S23.

Vincent C. Traynelis, "Prosthetics and Biologics: The Wave of the Future," Clinical Neurosurgery, vol. 50, Proceedings of the Congress of Neurological Surgeons, Philadelphia, PA 2002, Chapter 9, pp. 207-219.

Groh, et al., "Clinical Experience With the Dynesys Semirigid Fixation System for the Lumbar Spine," Spine, 2005, 30(3):324-331.

Holte et al., "Anterior lumbar fusion using a hybrid interbody graft," Eur. Spine J., 3:32-38, 1994, Exhibit No. 1014 in Case IPR2020-01310, U.S. Pat. No. 10,251,643.

Lane et al., "Transperitoneal Approach to the Intervertebral Disc in the Lumbar Area," Annals of Surgery, Mar. 1948, 127(3):537, Exhibit No. 1015 in Case IPR2020-01310, U.S. Pat. No. 10,251,643.

Michelson et al., "BAK/C Interbody Fusion System: A Threaded Cylindrical Cage for Cervical Fusion," Thieme Medical Publisher, Inc., New York, New York, 2005, 10 pages, Exhibit No. 1016 in Case IPR2020-01310, U.S. Pat. No. 10,251,643.

Prpa et al., "Lumbar Interbody Cages," Sug. Pro., Ch. 41, pp. 489-502, 2005, Exhibit No. 1017 in Case IPR2020-01310, U.S. Pat. No. 10,251,643.

Ryu and Kim, "Cervical Carbon Fiber Interbody Fusion Cage: Bengal System," Thieme Medical Publisher, Inc., New York, New York, 2005, 8 pages, Exhibit No. 1018 in Case IPR2020-01310, U.S. Pat. No. 10,251,643.

Schimmel et al., "PEEK Cages in Lumbar Fusion," Clin. Spine Surg., 29(5):E252-E258, Jun. 2016, Exhibit No. 1019 in Case IPR2020-01310, U.S. Pat. No. 10,251,643.

Synthes "SynFix-LR. Implant and instrumentation for standalone anterior lumbar interbody fusion (AALIF)," 2006, 26 pages, Exhibit No. 1020 in Case IPR2020-01310, U.S. Pat. No. 10,251,643.

Synfix, "EVOLUTION System," Online Product, DATE, 1 page, Exhibit No. 1021 in Case IPR2020-01310, U.S. Pat. No. 10,251,643.

Wagner et al., "Surgical Stabilization of the Equine Cervical Spine," Veterinary Surg., 8:1-6, Jan.-Mar. 1979, Exhibit No. 1023 in Case IPR2020-01310, U.S. Pat. No. 10,251,643.

Weiner and Fraser, "Spine Update Lumbar Interbody Cages," Spine, 23(5):634-640, 1998, Exhibit No. 1024 in Case IPR2020-01310, U.S. Pat. No. 10,251,643.

Wilke et al., "Primary stabilizing effect of interbody fusion devices for the cervical spine: an in vitro comparison between three different cage types and bone cement," Eur. Spine J., 2000, 9:410-416, Exhibit No. 1025 in Case IPR2020-01310, U.S. Pat. No. 10,251,643.

Wiseman et al., "Posterior Lumbar Interbody Fusion," Surgical Procedures, Ch. 39, 24 pages, Exhibit No. 1026 in Case IPR2020-01310, U.S. Pat. No. 10,251,643.

*Globus Medical, Inc.*, Petitioner v. *Moskowitz Family LLC*, Patent Owner Petition for Inter Partes Review of U.S. Pat. No. 10,251,643 Pursuant to 35 U.S.C. §§ 311-319 and 37 C.F.R. § 42, dated Jul. 21, 2020, 51 pages.

*Globus Medical, Inc.*, v. *Moskowitz Family LLC*, "Declaration of Jorge A. Ochoa, Ph.D., P.E.," Case IPR2020-01310, U.S. Pat. No. 10,251,643, dated Jul. 21, 2020, 57 pages (Exhibit No. 1003).

Auguste et al., "Expandable cylindrical cages in the cervical spine: a review of 22 cases," J. Neurosurg. Spine, 4:285-291, 2006, Exhibit No. 1006 in Case IPR2020-01310, U.S. Pat. No. 10,251,643.

Centinel Spine, [https://www.centinelspine.com/corp_producthistory.php, Retrieved on Jun. 4, 2020 11:48:58 PM], 7 pages, Exhibit No. 1009 in Case IPR2020-01310, U.S. Pat. No. 10,251,643.

Dickman, "Internal Fixation and Fusion of the Lumbar Spine Using Threaded Interbody Cages,". [https://www.barrowneuro.org/education/grand-rounds-publications-and-media/barrow-quarterly/, Retrieved on Jun. 20, 2020], 41 pages, Exhibit No. 1010 in Case IPR2020-01310, U.S. Pat. No. 10,251,643.

Dryer, "Affinity Anterior Cervical Cage System," Thieme Medical Publisher, Inc., New York, New York, 2005, 9 pages, Exhibit No. 1011 in Case IPR2020-01310, U.S. Pat. No. 10,251,643.

Folman et al., "Posterior Lumbar Interbody Fusion for Degenerative Disc Disease Using a Minimally Invasive B-Twin Expandable Spinal Spacer," Journal of Spinal Disorders & Techniques, Oct. 2003, 16(5):455-60, Exhibit No. 1012 in Case IPR2020-01310, U.S. Pat. No. 10,251,643.

Guyer and Ohnmeiss, "Degenerative Disc Disease: Fusion Cages and Dowels," Lippincott Williams & Wilkins, Philadelphia, PA, 2004, Ch. 35, 12 pages, Exhibit No. 1013 in Case IPR2020-01310, U.S. Pat. No. 10,251,643.

(56) References Cited

OTHER PUBLICATIONS

Synthes "SynFix-LR. Implant and instrumentation for standalone anterior lumbar interbody fusion (ALIF)," 2006, 26 pages, Exhibit No. 1020 in Case IPR2020-01310, U.S. Pat. No. 10,251,643.

* cited by examiner

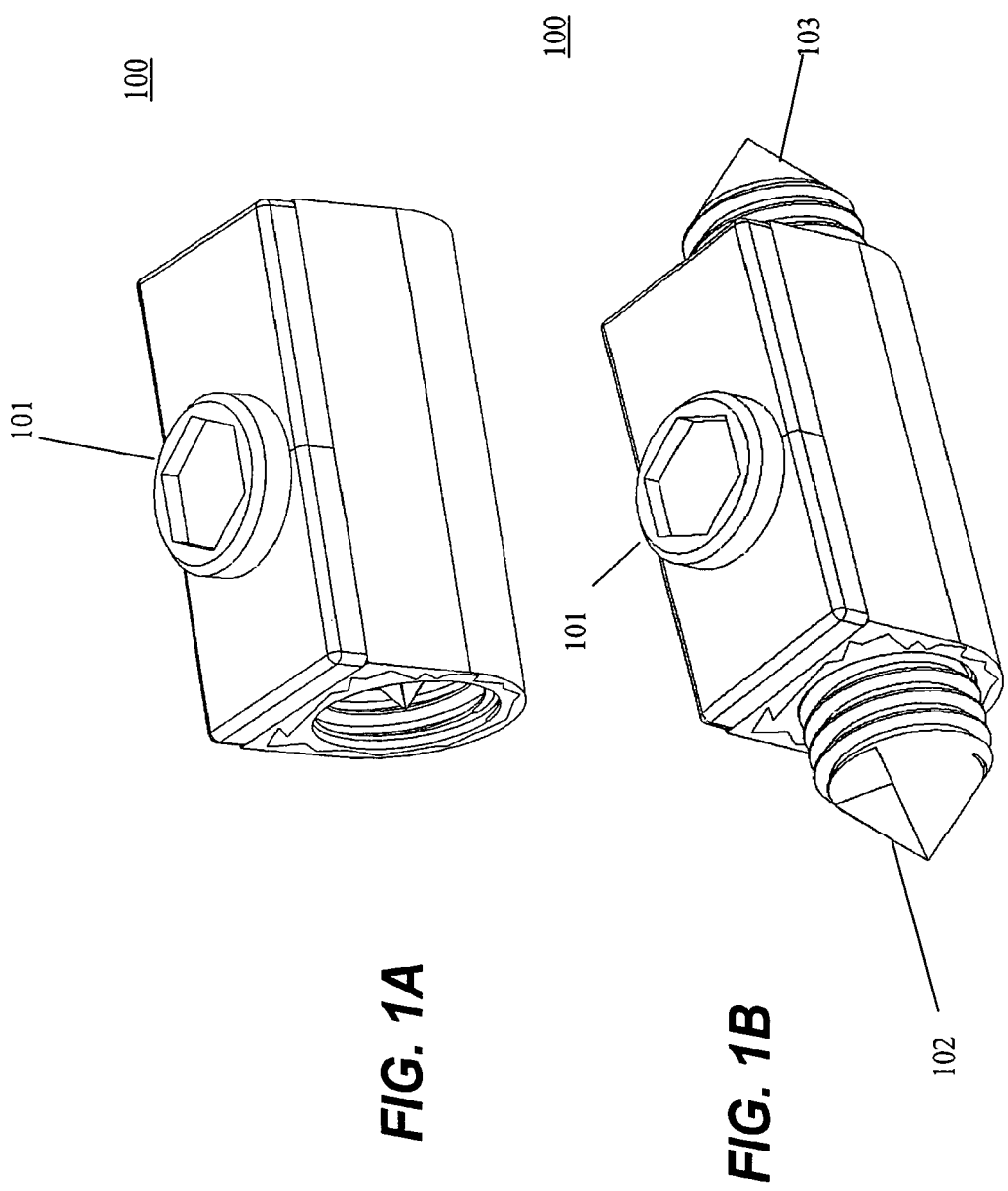

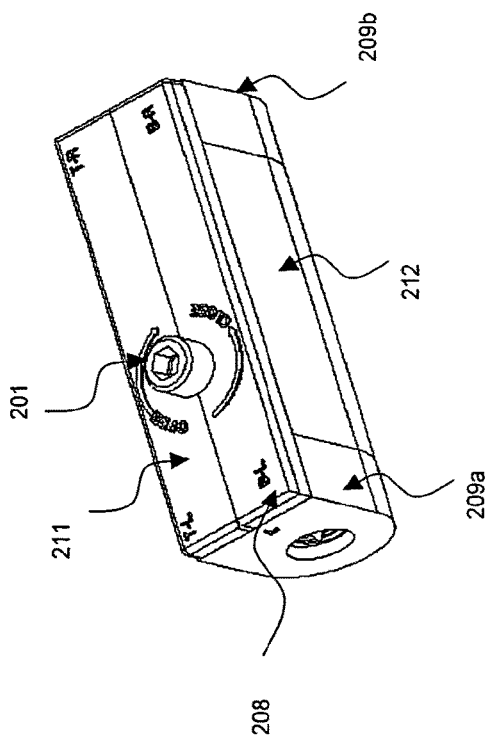
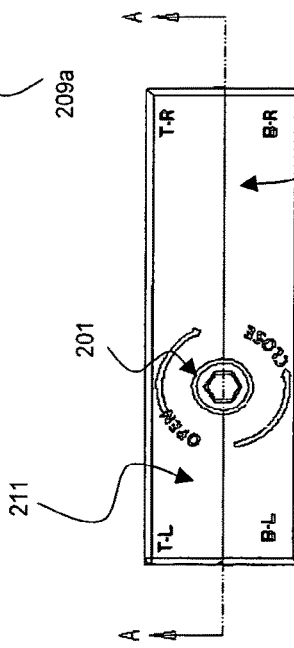
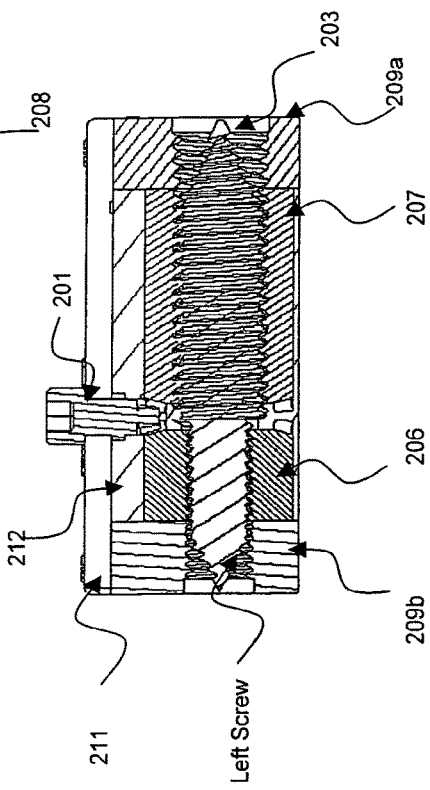
FIG. 2A
FIG. 2B
FIG. 2C

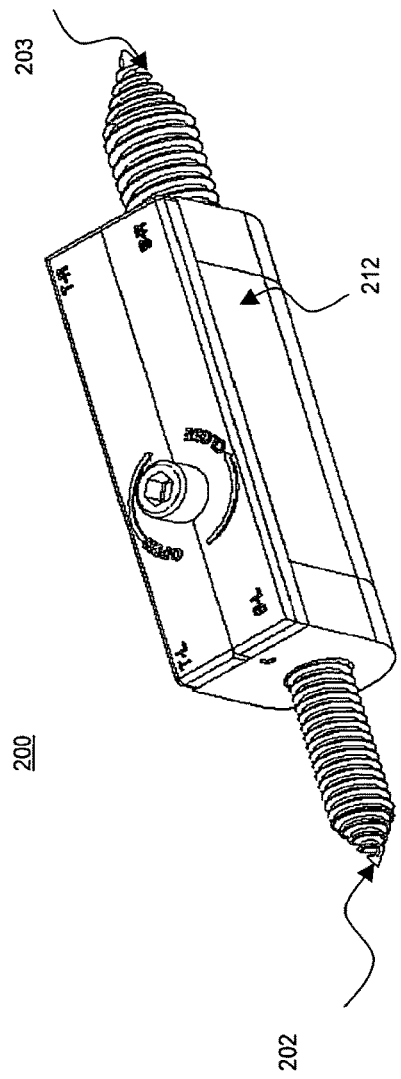
FIG. 2D
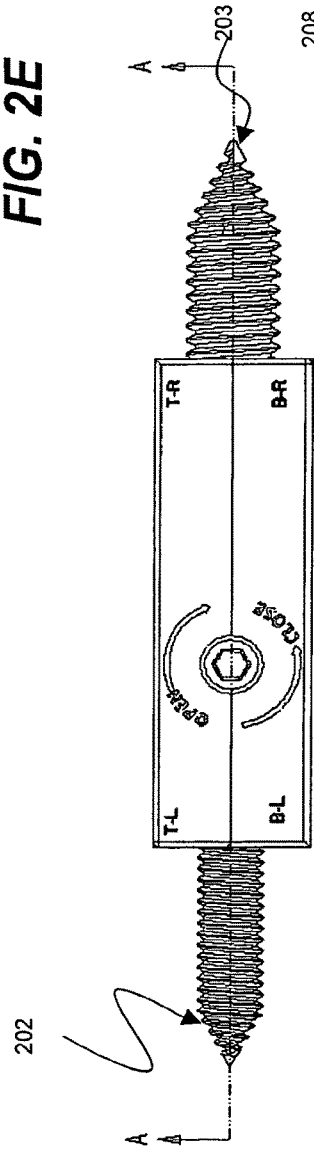
FIG. 2E
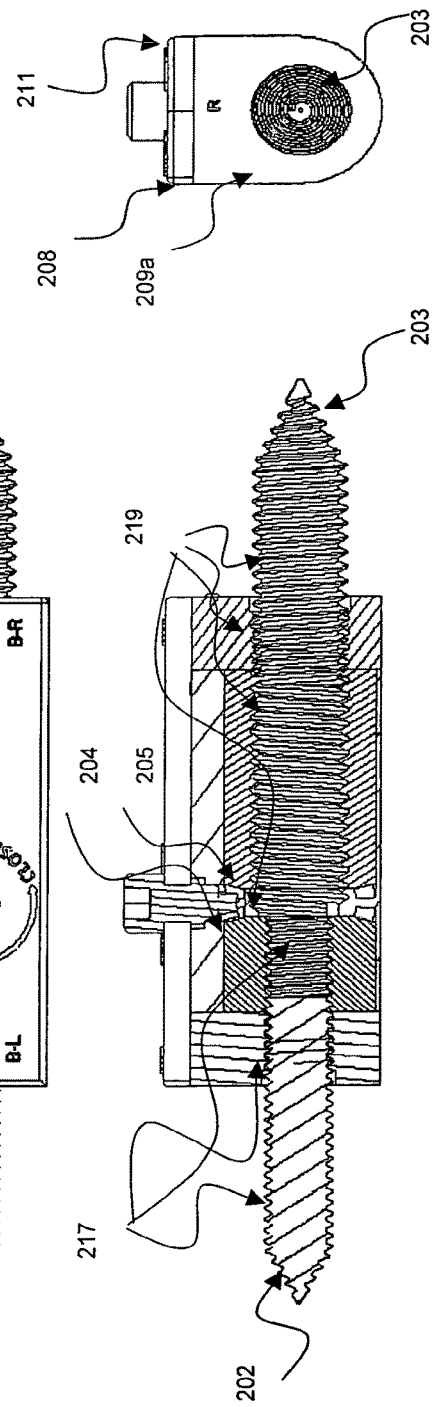
FIG. 2G
FIG. 2F

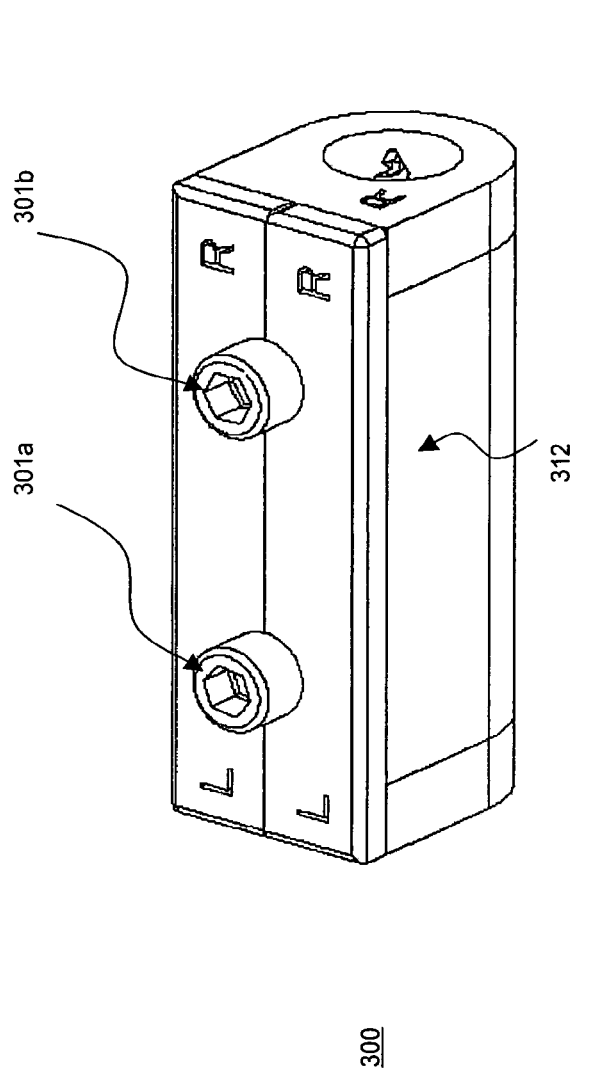
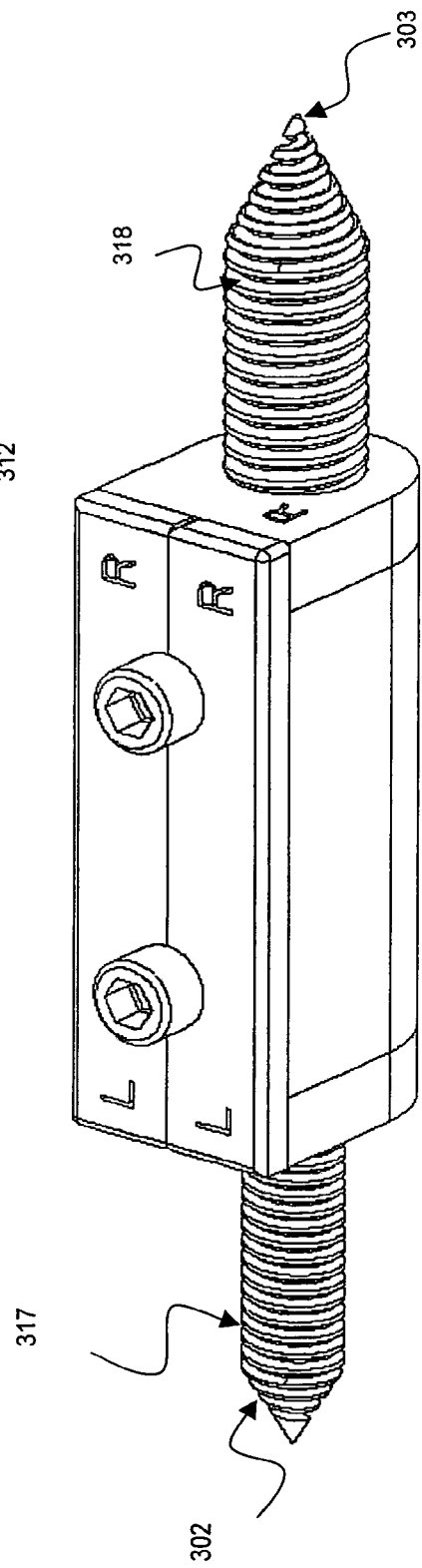
FIG. 3A
FIG. 3B

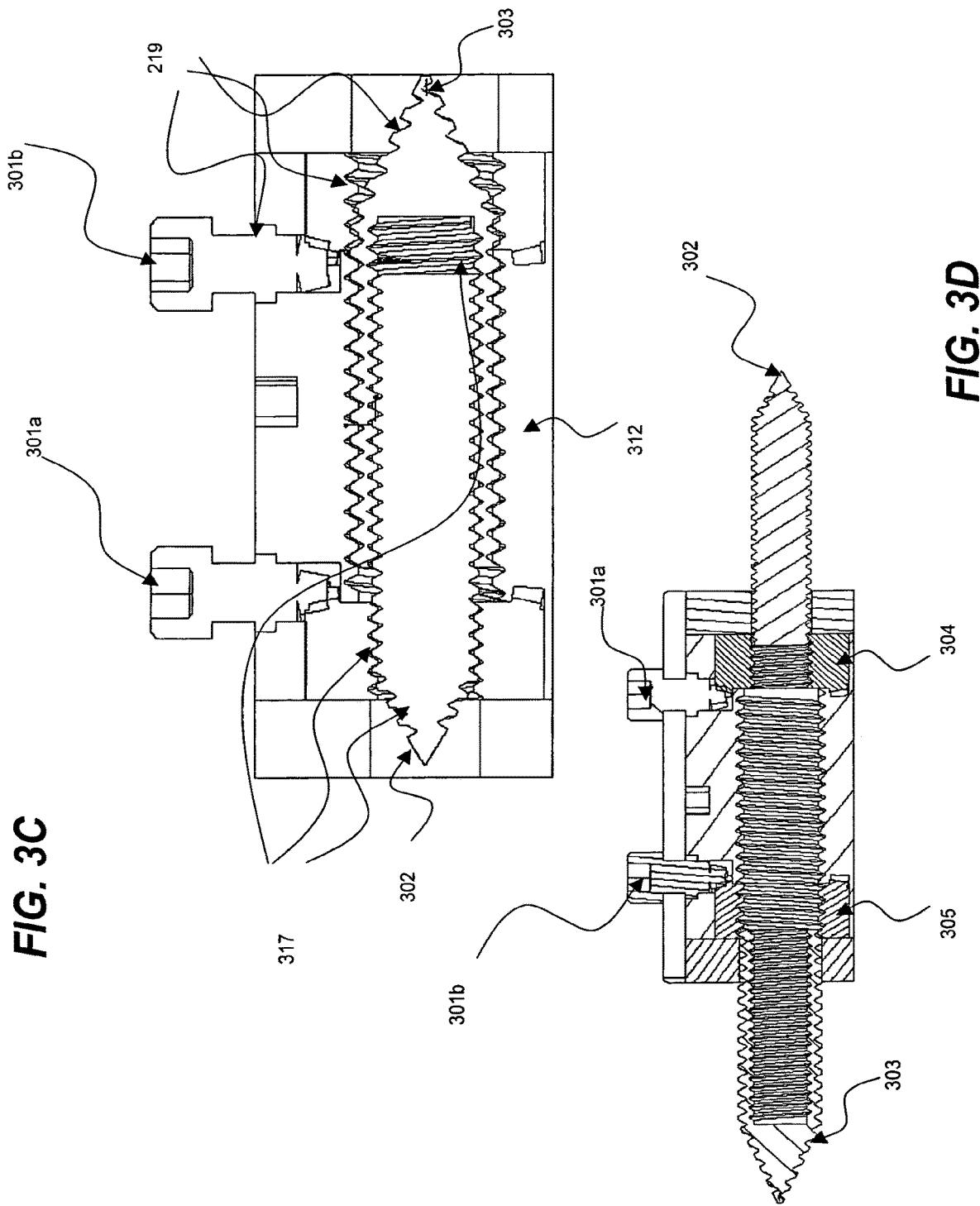

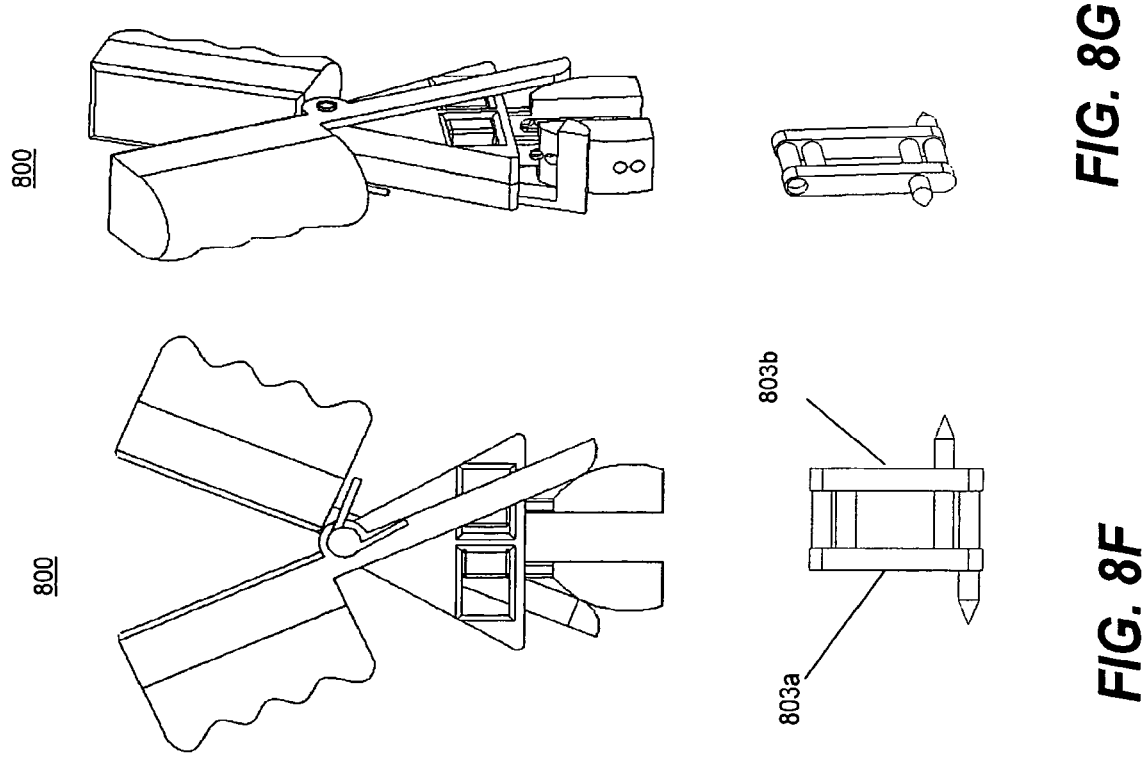

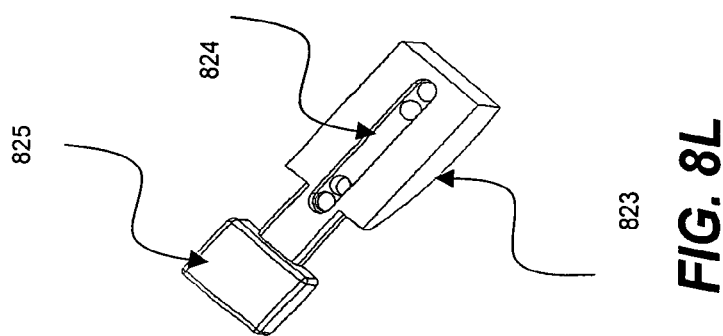
FIG. 8L
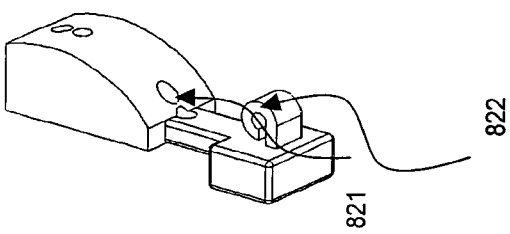
FIG. 8K
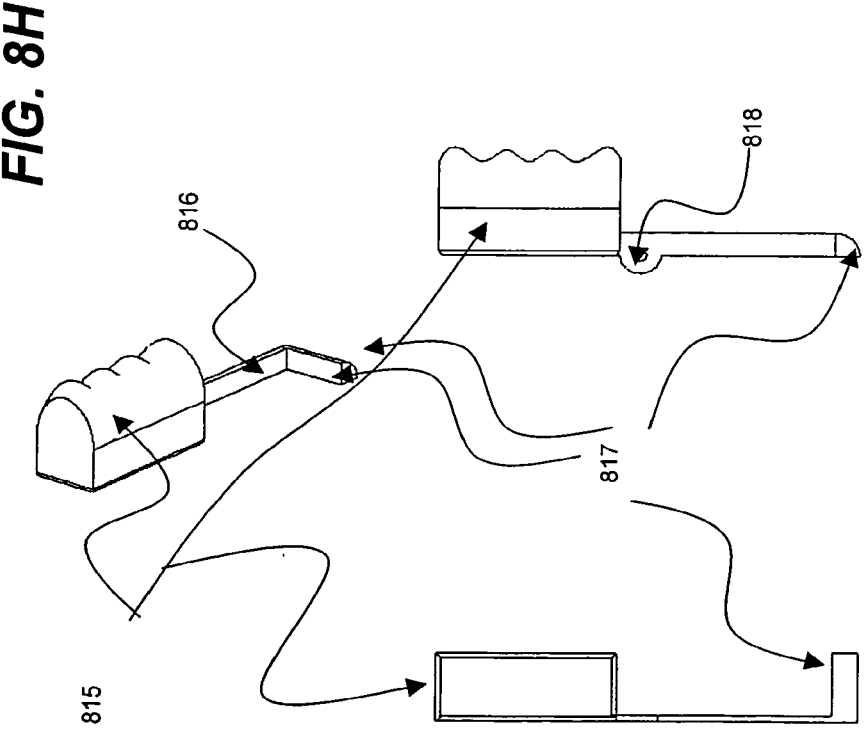
FIG. 8H
FIG. 8J
FIG. 8I

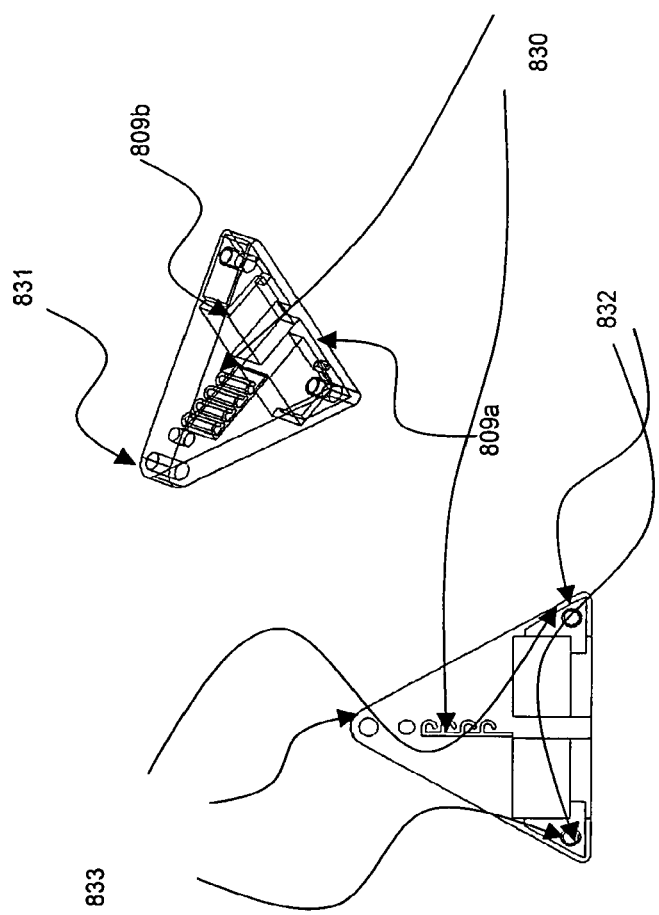

ARTIFICIAL INTERVERTEBRAL IMPANT

CROSS-REFERENCE TO RELATED APPLICATIONS

This application is a continuation of U.S. application Ser. No. 15/934,622, filed Mar. 23, 2018, (now U.S. Pat. No. 10,251,643) which is a continuation of U.S. application Ser. No. 13/093,812, filed Apr. 25, 2011 (now U.S. Pat. No. 9,924,940), which is a continuation of U.S. application Ser. No. 12/347,990, filed Dec. 31, 2008 (now U.S. Pat. No. 7,951,180), which is a divisional of U.S. application Ser. No. 11/208,644, filed Aug. 23, 2005 (now U.S. Pat. No. 7,704,279), which claims the benefit of Provisional Application No. 60/670,231, filed on Apr. 12, 2005, the entire contents of which is incorporated herein by reference.

FIELD OF INVENTION

The present invention relates to bi-directional fixating transvertebral (BDFT) screws which can be used to supplement other intervertebral spacers and/or bone fusion materials. BDFT screws can be incorporated into anterior and/or posterior cervical and lumbosacral novel zero-profile horizontal and triangular intervertebral mini-plates. In addition BDFT screws can be incorporated into two dimensional, expansile intervertebral body fusion devices (IBFDs) transforming them into stand-alone posteriorly and/or anteriorly placed cervical, thoracic and lumbar spinal fusion devices. In the lumbosacral and thoracic spine BDFT screws may obviate the need for supplemental pedicle screw fixation. In the cervical spine it obviates the need for supplemental vertically oriented anterior plating. The present invention also relates to a stand-alone or supplemental, calibrating interarticular joint stapling device which can incrementally fine-tune posterior interarticular joint motion.

DESCRIPTION OF THE RELEVANT ART

Segmental spinal fusions which stabilize two or more adjacent segments of the spine are performed for painful degenerative disc disease, recurrent disc herniations, spinal stenosis, spondylolysis and spondylolisthesis. Over the past several decades a wide variety of fusion techniques and instrumentation have evolved. One of the earliest posterior fusion techniques entails non-instrumented in-situ on-lay posteriolateral fusion utilizing autologous iliac crest bone. Because of the high rate of imperfect fusions i.e. pseudoarthroses, transpedicular pedicle screw fixation which utilizes a variety of rods and interconnectors were developed to achieve less interbody motion and hence higher fusion rates. Pedicle screw fixation was initially combined with on-lay posteriolateral fusion. Because of the poor blood supply of the transverse processes, issues still remained with pseudoarthroses. In an attempt to address this problem, pedicle screw fixation has been supplemented with a variety of interbody fusion devices. This is based on the concept that axial loading enhances fusion and that the vertebral endplates have a better blood supply. Interbody lumbar fusion devices can be placed anteriorly via an anterior lumbar interbody fusion technique (ALIF) or posteriorly via a posterior lumbar interbody fusion technique (PLIF). Material options for interbody fusion devices have included autologous iliac crest/laminar bone, cylindrical threaded titanium interbody cages, cylindrical threaded cortical bone dowels, vertebral interbody rings or boxes, carbon fiber cages, or femoral ring allograft. To lessen the complication of prolonged nerve root retraction the technique of circumferential tansforaminal lumbar interbody fusion technique (TLIF) has been introduced. This employs the transforaminal placement of an interbody spacer such as one kidney bean shaped allograft, two circular allografts, one or two titanium circular cages, a single titanium or Peek (polyether-ketone) boomerang spacer. The threaded spacers are usually supplemented with autologous bone and/or bone morphogenic protein (BMP), demineralized bone matrix (DBM) in the form of paste or cement, rh-BMP with collagen sponges, or similar osteoinductive biological agents which are known to enhance fusion.

Currently all lumbosacral fusion techniques, ALIF, PLIF and TLIF, are typically supplemented by pedicle screw placement. In addition posterior transfacet screws also have been used to supplement ALIF procedures. Complications of pedicle screw placement include duration of procedure, significant tissue dissection and muscle retraction, misplaced screws with neural and/or vascular injury, excessive blood loss, need for transfusions, prolonged recovery, incomplete return to work, excess rigidity leading to adjacent segmental disease requiring further fusions and re-operations. Further advances of pedicle screw fixation including minimally invasive and image-guided technology, and the development of flexible rods have imperfectly addressed some but not all of these issues. Transfacet screws entail the use of long screws which provide a static facet alignment without motion calibration.

Complications of all current interbody fusion devices is their lack of coverage of the majority of the cross sectional area of the vertebral endplates and their potential for extrusion. The recently described flexible fusion system which consists of flexible rods attached to transpedicular screws (Dionysis, Zimmer) suffers from a high pull-out rate, higher rate of re-operation than standard fusions, and does not rank high with patient satisfaction. See for example, Clinical experience with the Dynesys semirigid fixation system for the lumbar spine: Surgical and patient-oriented outcome in 50 cases after an average of 2 years; D, Grob, A. Benini and A. F. Mannion. Spine Volume 30, number 3, Feb. 1, 2005.

Single or multiple level anterior cervical spinal fusions typically employ the replacement of the cervical disc or discs with autologous or allograft bone, or an intervertebral spacer filled with autologous or allograft bone, demineralized bone matrix, BMP or rh-BMP etc. Currently these anterior cervical fusions are augmented with anterior vertical titanium plates which cross the intervertebral space or spaces and are secured to the vertebral bodies above and below the disc space or spaces with perpendicularly penetrating vertebral body screws. The purpose of these plates is to serve as a barrier to prevent extrusion of the intervertebral disc replacement. Recently anterior vertical plating has also been employed in anterior lumbar fusion.

Complications of anterior spinal plating include the potential for neurovascular injury with screw misplacement, screw and/or plate pull-out, and screw and/or plate breakage. Other complications include potential esophageal compression/injury in the cervical spine secondary to high plate profile or pullout, and to potential devastating vascular injury in the lumbar spine with plate movement and/or dislodgement into anterior iliac vasculature. Recent advances in cervical plating have therefore concentrated on the creation of lower profile plates and even resorbable plates. These advances, however, have not eliminated the-possibility of plate dislodgement and screw back out/breakage.

To achieve segmental fusion applicants propose the use of novel bidirectional fixating transvertebral (BDFT) screws which can be strategically inserted via anterior or posterior surgical spinal approaches into the anterior and middle columns of the intervertebral disc space. The BDFT mechanism employs turning one or two pinions which then turns one or two central gears which in turn simultaneously controls expansile movement of right and-left-handed bi-directional screws. The vertebral bodies above and below the disc space by virtue of their engagement and penetration by the BDFT screws are thus linked and eventually fused. The casings of the BDFT screws prevent vertebral body subsidence. The inside of the denuded intervertebral space can then be packed with autologous or allograft bone, BMP, DBX or similar osteoinductive material. Alternatively an intervertebral spacer filled with either of these substances can be inserted.

Applicants postulate that BDFT screws provide as strong or stronger segmental fusion as pedicle screws without the complications arising from pedicle screw placement which include screw misplacement with potential nerve and/or vascular injury, violation of some healthy facets, possible pedicle destruction and blood loss. By placing screws across the intervertebral space from vertebral body to vertebral body engaging anterior and middle spinal columns, and not into the vertebral bodies via the transpedicular route, some of the healthy facet joints are preserved. Because this technique accomplishes both anterior and middle column fusion, without rigidly fixing the posterior column, it in essence creates a flexible fusion. This device therefore is a flexible fusion device because the preserved posterior joints retain their function achieving at least a modicum of mobility and hence a less rigid (flexible) fusion.

The very advantage of trans-pedicular screws which facilitate a strong solid fusion by rigidly engaging all three spinal columns (anterior, middle and posterior), is the same mechanical mechanism whereby complete inflexibility of all columns is incurred thereby leading to increasing rostral and caudal segmental stress which leads to an increased rate of re-operation.

Transvertebral fusion also leads to far less muscle retraction, blood loss, and significant reduction in O.R. time. Thus the complication of pedicular screw pull-out and hence high re-operation rate associated with the current embodiment of flexible fusion pedicle screws/rods is obviated. The lumbosacral BDFT screws can be introduced via PLIF, TLIF or ALIF operative techniques. Although one can opt to supplement these screws with transpedicular screws there would be no absolute need for supplemental pedicle screw fixation with these operative techniques.

Bi-directional fixating transvertebral (BDFT) screws can also be combined with novel zero-profile horizontal cervical and lumbar mini-plates. They can also be combined with mini-plates and a cage with slots for bone material insertion. Thus this is in essence a three-in-one device; 1) cage which can be filled with bone, 2) a plate and 3) BDFT screws.

For the performance of anterior cervical, and lumbar anterior or posterior fusions one or two centrally placed BDFT screws anterior to an intervertebral graft or spacer, may be a sufficient barrier by itself to prevent device/graft extrusion. However, to further safeguard against graft/spacer extrusion applicants have devised horizontal linear mini-plates which can be incorporated into two anteriorly placed BDFT screws, as well as a linear triangulating mini-plate which can be incorporated into two anteriorly placed, and one posteriorly placed BDFT screws. The horizontal linear mini-plates or horizontal triangular mini-plate traverse the diameter of the disc space and most of the disc space height. Thus a horizontal mini-plate placed anteriorly immediately beneath the rostra! and caudal ventral vertebral body surfaces which is secured by BDFT screws which are also beneath the vertebral body surfaces, would prevent intervertebral device/graft extrusion. This mini-plate is essentially a zero- to subzero-profile plate in that it is either flush with the vertebral body surfaces or below them.

Because the BDFT screws engage a small percentage of the rostra! and caudal vertebral bodies, this plating system could be performed at multiple levels. This plating system which utilizes BDFT screws does not lead to any esophageal compression or injury in the cervical spine or vascular iliac vein injury in the lumbar spine. For the performance of two or three level intervertebral fusion with horizontal mini-plates there is virtually no possibility of plate breakage which can occur in long vertical anterior plates which are in current usage. Similarly, screw dislodgement, if it occurs would lead to minimal esophageal compression or injury compared to large vertical plate/screw dislodgement. In addition, in the cervical spine BDFT screw placement closer to the midline would avert any possibility of lateral neural or vertebral artery injury.

In copending PCT Patent Application PCT/US2005/016493, filed May 11, 2005, the entire contents of which are incorporated by reference, applicants developed an interbody expansile artificial disc device composed of an inner core artificial disc surrounded by expansile titanium shells with spikes which can expand in two or three dimensions. In yet another embodiment of tranvertebral fixation applicants propose a novel cervical and thoracic/lumbosacral intervertebral fusion device (IBFD) which combines the expansile titanium or PEEK shells or our previous artificial disc design with BDFT screws which can be inserted into the disc space.

Yet another embodiment incorporates a core expansile elastometric porous balloon sheath vulcanized to the expandable external shells which can then be filled with bone fusion material. Balloon porosity would allow fusion to occur from vertebral endplate to endplate. Bony material can be injected into this porous balloon through a port directly or through a silastic catheter (see previous patent).

If one were inclined to further enhance posterior column thoracolumbosacral fixation, applicants introduce an optional novel calibrated facet stapling device which staples the inferior articulating facet of the superior segment to the superior articulating facet of the caudal vertebral segment unilaterally or bilaterally, further minimizing motion until interbody fusion occurs. The degree of flexibility can be further modulated by varying the calibration strength and torque of facet stapling. This would be dictated by the need for greater or lesser degrees of motion preservation.

Currently, failed anterior lumbar arthoplasties are salvaged by combined anterior and posterior fusions. BDFT screws and/or IBFDs could be utilized as a one-step salvage operation for failed/extruded anteriorly placed lumbar artificial discs obviating the above salvage procedures which have greater morbidity. Likewise, for anterior cervical fusion, applying cervical BDFT screws alone or in combination with cervical mini-plates addresses the deficiencies and complications of current cervical plating technology as mentioned above.

BRIEF DESCRIPTION OF THE DRAWINGS

FIGS. 1A-D illustrate three-dimensional and cross-sectional views of the BDFT screw and its mechanism of operation (Embodiment I).

FIGS. 2A-G illustrate three-dimensional and cross-sectional views of the BDFT screw and its mechanism of operation (Embodiment II).

FIGS. 3A-E illustrate three dimensional, cross-sectional and exploded views of the BDFT screw and its mechanism of operation (Embodiment III).

DETAILED DESCRIPTION OF THE INVENTION

1. The Medical Device

Figure 1C:
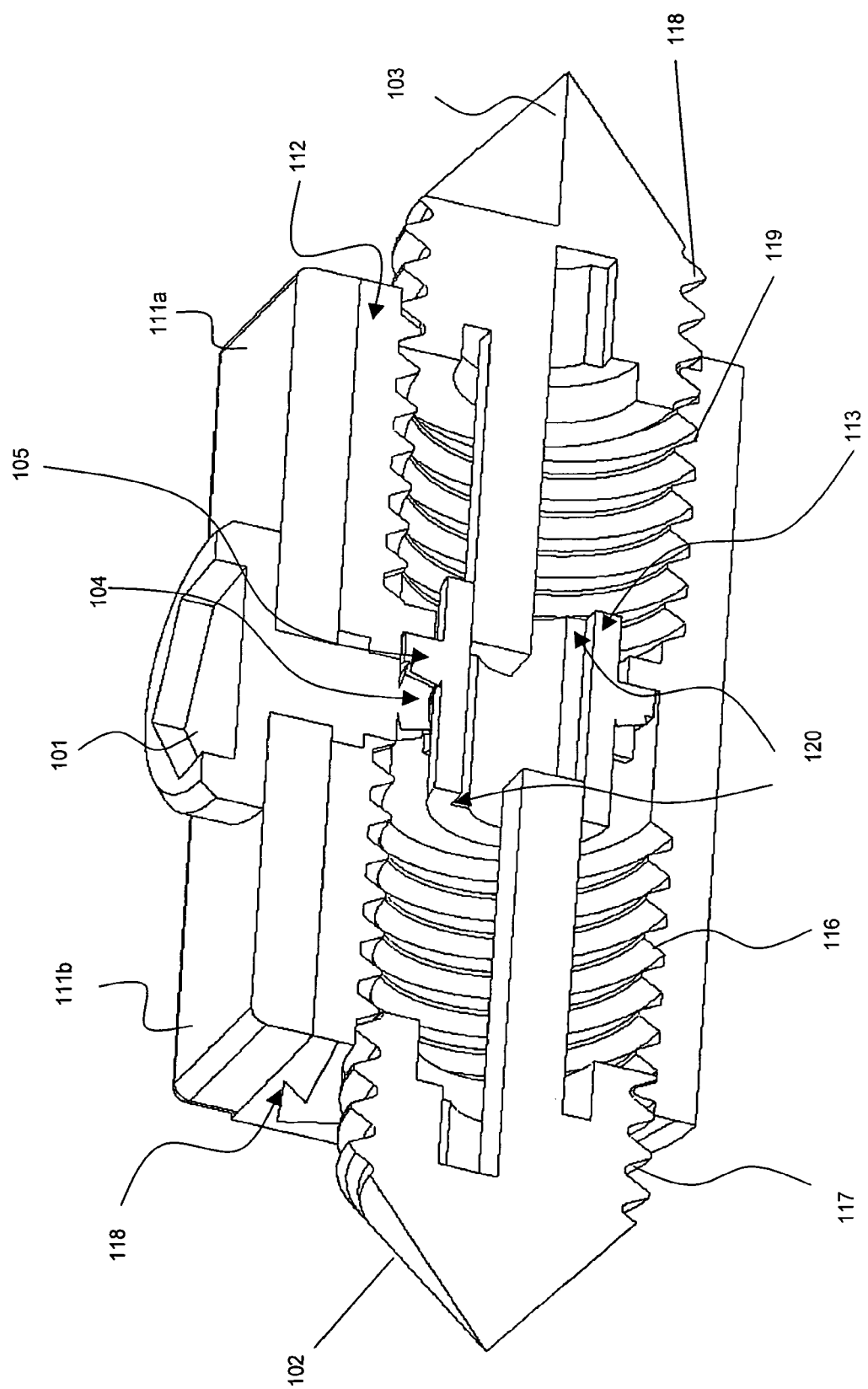
Figure 1D:
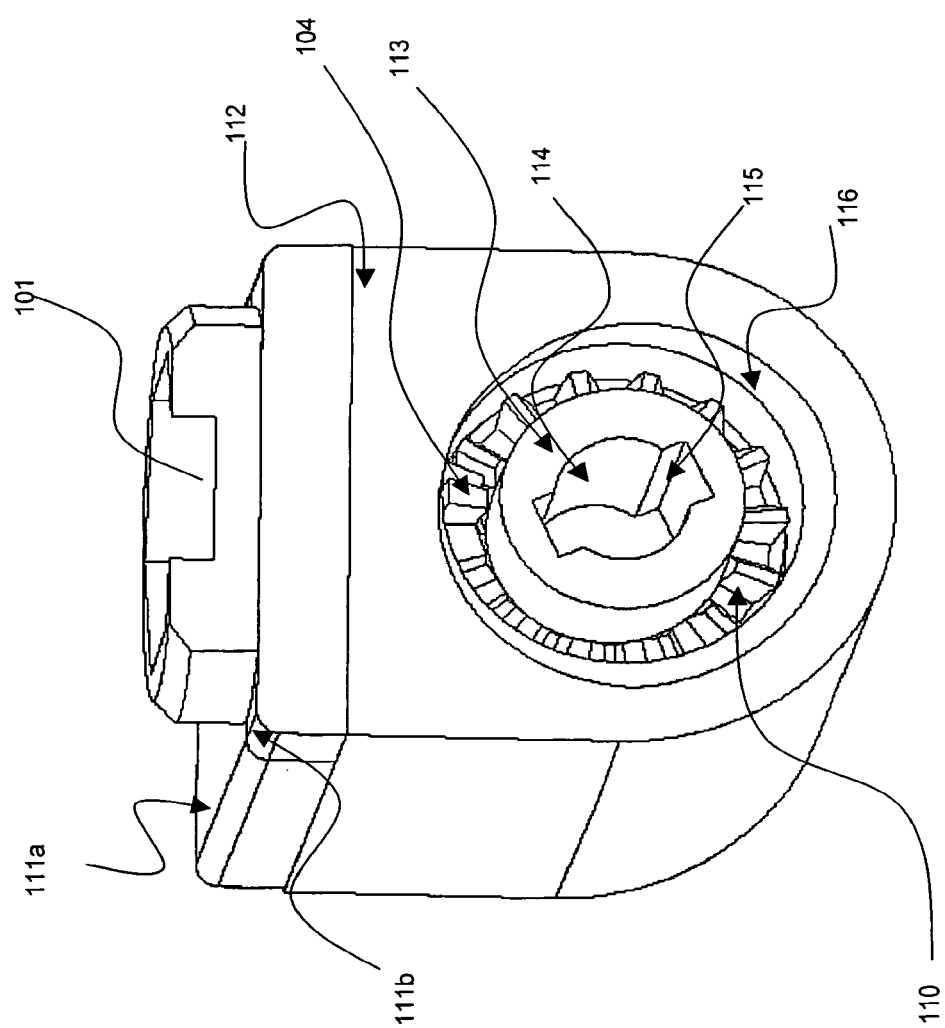
Figure 3E:
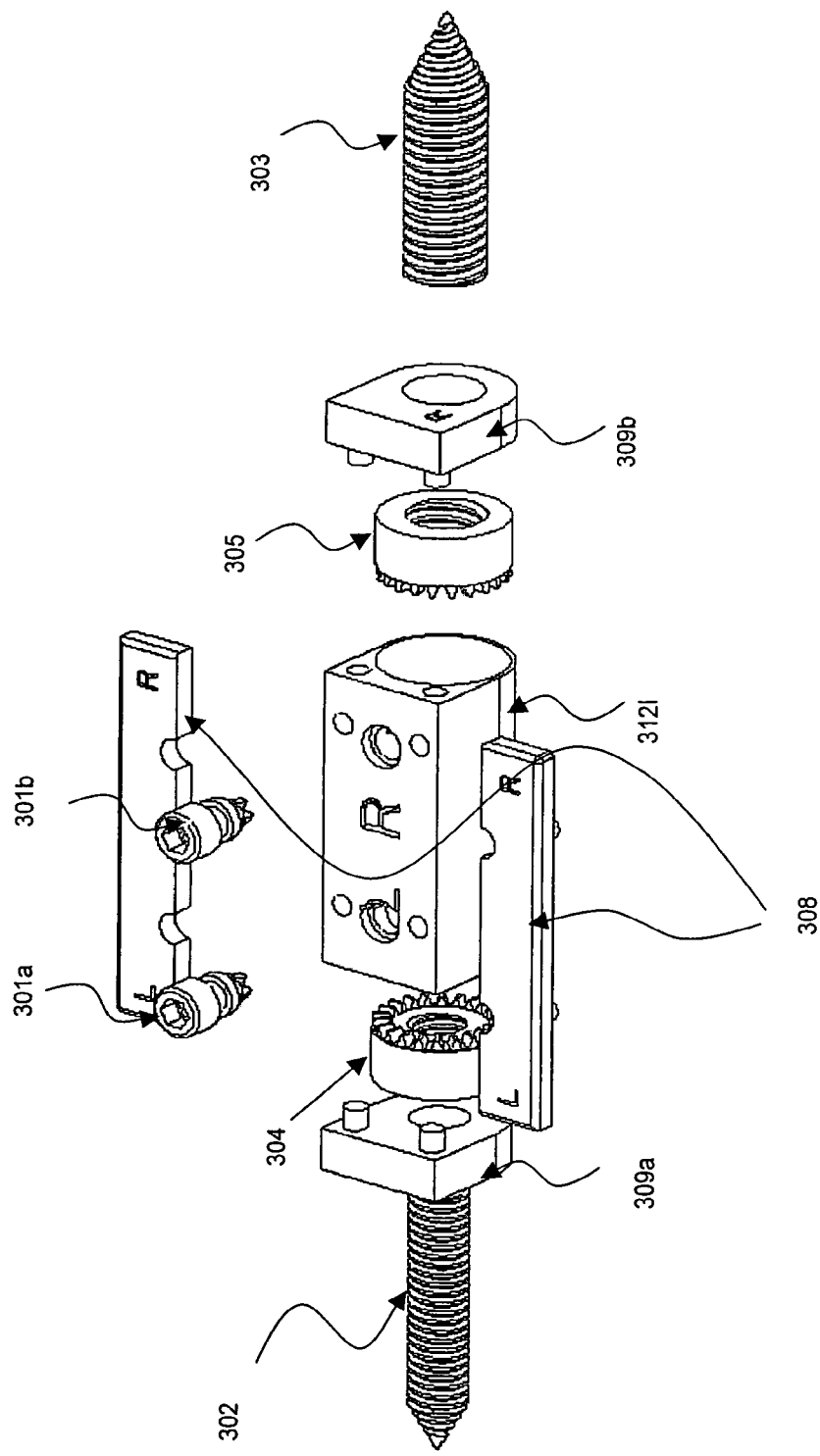

Referring to FIGS. 1A-D the above described problem can be solved in the cervical, thoracic and lumbar spine by insertion into the denuded intervertebral disc space an expansile bi-directional fixating transvertebral (BDFT) screw 100 or screws.

FIGS. 1A and 1B illustrate three-dimensional views of the screw 100 in closed and opened positions, respectively, upon its insertion into the intervertebral disc space. The screw 100 is self-drilling. The mechanism of its action entails the turning of a midline drive screw 100/pinion 104 in a clock-wise direction. This motion is bi-directionally translated via an interposing gear mechanism 105 enabling the simultaneous outward movement of left and right handed screws 102, 103 in equal and opposite directions. When the drive screw 101 and its accompanying drive screw shaft are turned clock-wise, the driving pinion 104 is likewise rotated. This motion is then translated to the driven gear 105 which is interposed between the drive screw 101 and two opposing self-drilling screws 102, 103, one left-handed and the other right-handed. The gear ring 110 has screw coupling slots (Figures IC and 1D). There are also symmetric keyways 120 and an alignment cylinder 113. The left handed screw 102 fits into one half of the slots 114, 115 and the right handed screw 103 into the other half of the slots. This is clearly illustrated in cross sections of the screw and gear in Figures IC and ID, respectively.

FIGS. 1A-C also illustrate the external casing 111 of the device which contains the external screw threads 117, 118, against which the left and right handed internal threads interact 116, 119 with. The casing includes an upper left casing 111b and an upper right casing 111a. Below the upper casing 111b there is a surface serration pattern 118 which is part of a retaining outer shell 112.

FIGS. 2A-G illustrate Embodiment II of the BDFT 200. This design differs in two fundamental ways from Embodiment I. Firstly the driving pinion 201 accomplishes bi-directional movement by engaging left and right gears 204, 205 which simultaneously turn left and right screws 202, 203 (FIGS. 2C-G). Secondly, in it's resting closed position the solid left screw 202 with a narrower diameter is buried within the right wider diameter hollow right screw 203. This mechanism allows for greater length of screw expansion compared to Embodiment I. Maintaining alignment of screws 202, 203 and pinions 201 is accomplished by upper casings 211, outer shells 212, and left and right screw caps 209a, 209b (FIGS. 2A-G).

FIGS. 3A-E illustrate Embodiment III of the BDFT 300. This is similar to Embodiment II. The major difference is the use of two separate driving screws pinions 301a, 301b for the two separate gears 304, 305. There is one pinion 301a for the left screw 302 and another pinion 301b for the right screw 303. The left screw 302 engages the left gear 304 which engages the left screw 302. The right pinion 301a engages the right gear 305 which engages the right screw 303. Because the left and right screws 302, 303 have separate controls and are not linked by one common pinion, separate distinct motions of the screws 302, 303 can be obtained, as opposed to equal and simultaneous screw movements of Embodiments I and II. Like Embodiment II, Embodiment III consists of a smaller diameter solid left screw 302 which fits into a larger diameter hollow right screw 303. This can achieve significant screw extension length as in Embodiment II.

Figure 4A:
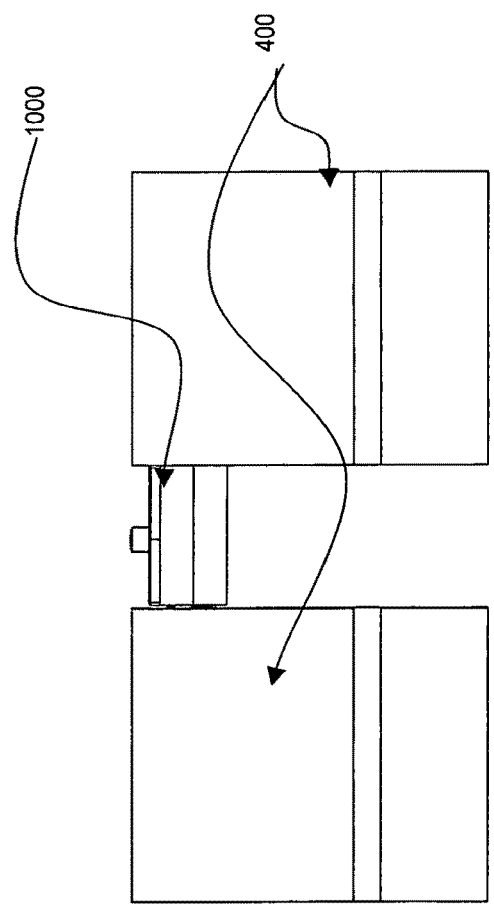
FIGS. 4A-C illustrate a single or three BDFT screws inserted into adjacent vertebral bodies.
Figure 4B:
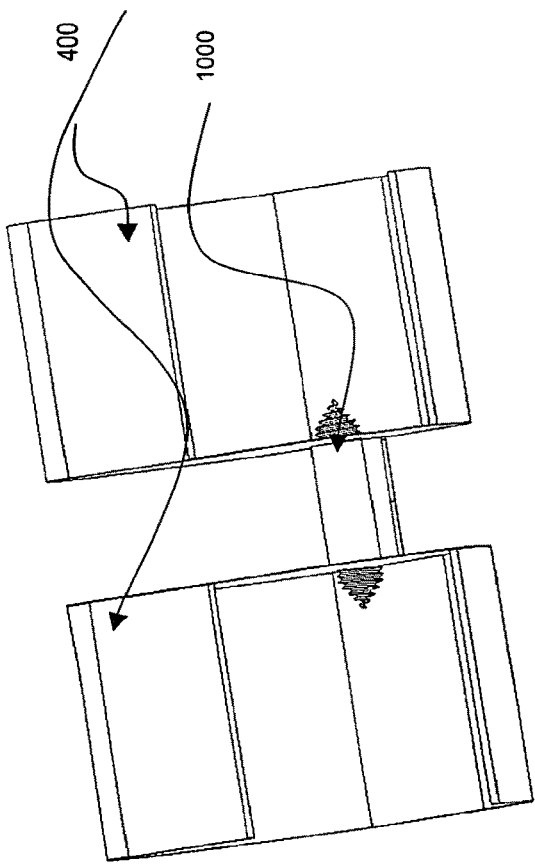

FIGS. 4A and 4B illustrates the placement of a single BTFD 1000 screw anteriorly into the intervertebral space between adjacent lumbar vertebrae 400. FIG. 4A illustrates the closed position. FIG. 4B illustrates the opened position. The illustrations are of a generic BDFT screw 1000 i.e. it applies to Embodiments I-III. Placement of a single BDFT anterior to an intervertebral spacer may be sufficient to prevent interspacer/device extrusion, and enhance spinal stability.

Figure 4C:
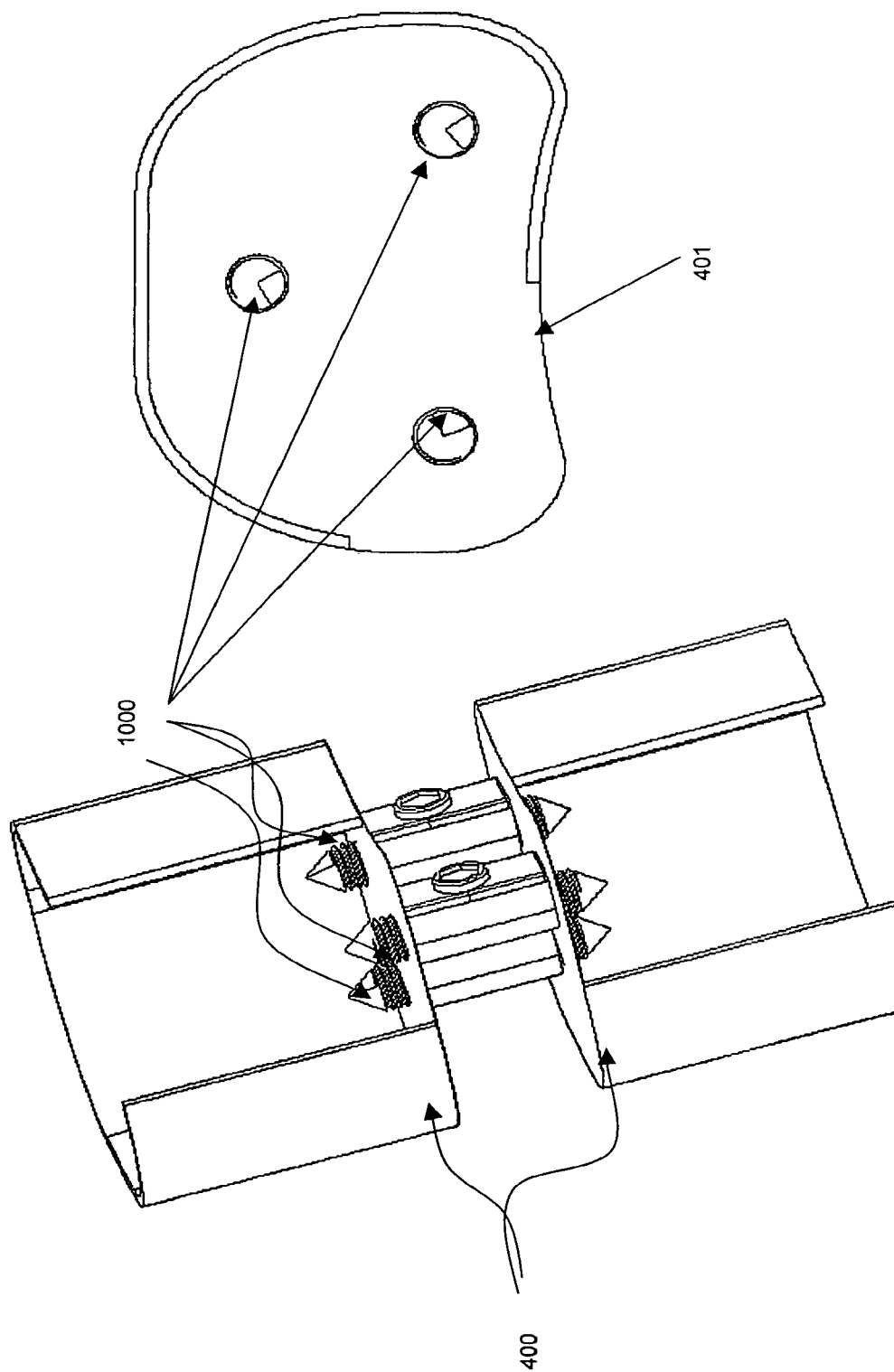

FIG. 4C illustrates the placement of three BTFD screws 1000 in a triangulating manner covering anterior and middle columns. The presence of three screws so situated would prevent subsidence of the screws 1000. Hence they act as a very open IBFD 1000. Bone material in the form of DBX or BMP etc. could be inserted into the intervertebral space in between the three screws 1000. This construct could be used as a supplemental or stand alone intervertebral fusion device. Also illustrated is a cross-section of a vertebral endplate 401 demonstrating the triangular placement of screws 1000 engaging anterior and middle columns.

Figure 5B:
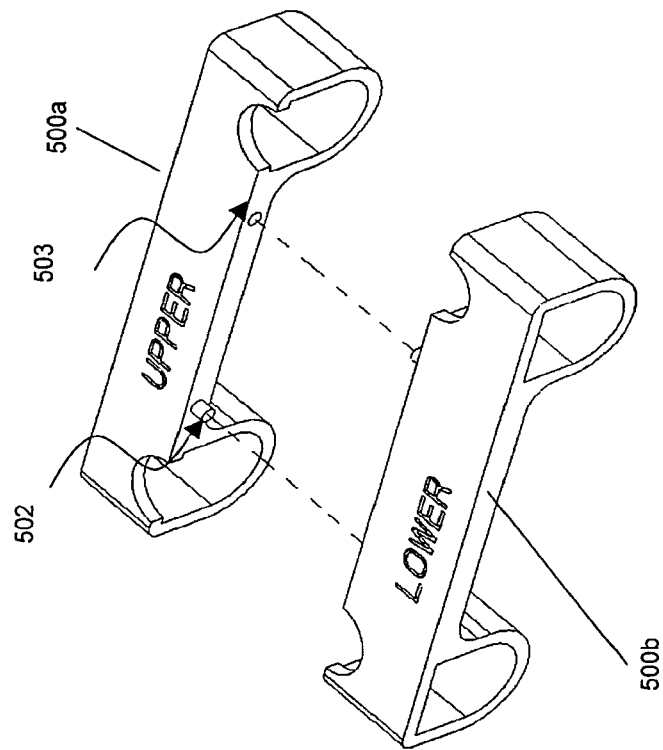
FIGS. 5A and 5B illustrate three-dimensional views of the zero-profile linear mini-plate.
Figure 5A:
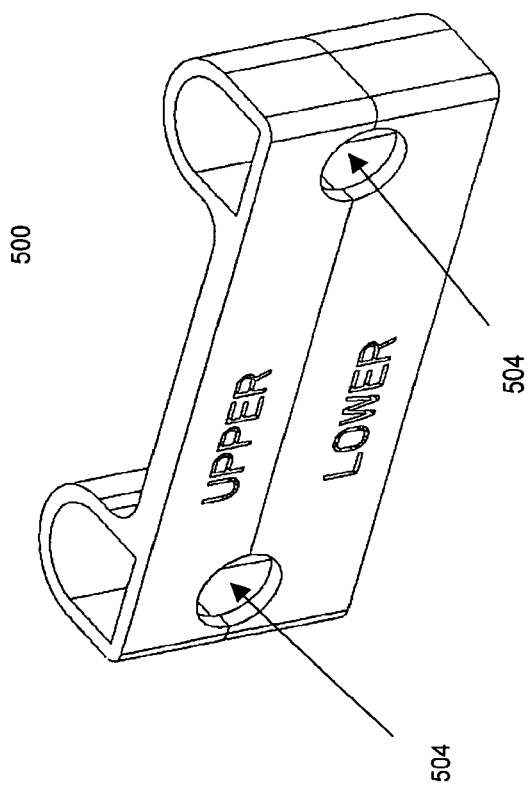
Figures 5C, 5D:
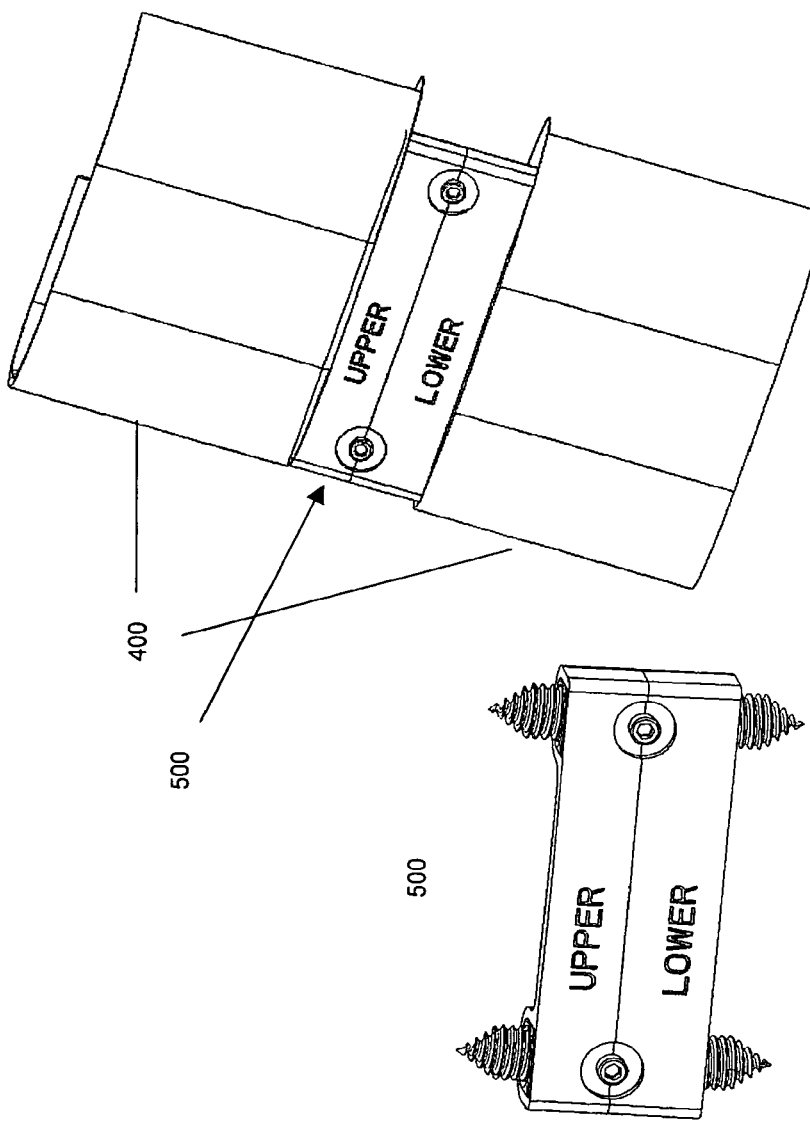
FIGS. 5C and 5D illustrate the integration of BDFT screws in the zero-profile linear mini-plate.

FIG. 5A illustrates the zero-profile horizontal linear mini-plate 500. Note the slots for placement of the BDFT screws 1000. On the anterior surface are slots 504 for the driving pinion screws. FIG. 5B illustrates that the plate 500 consists of upper and lower portions 500a, 500b which articulate with each other via interdigitation of alignment pins 502 and recesses 503. FIG. 5C illustrates the integration of the BDFT screws 1000 into the mini-plate 500. FIG. 5D illustrates the placement of the plate-BDFT construct into the intervertebral space. After the construct is placed into the intervertebral space, the screws 1000 are expanded bi-directionally in order to engage the vertebral bodies 400. This construct can be surgically placed via anterior or posterior approaches.

FIGS. 6A-G illustrate a zero-profile triangular mini-plate 600. In this embodiment the plate encompasses all three triangularly situated BDFT screws 1000. The posteriorly placed BDFT screw 1000 is expanded with a centrally placed drive screw/pinion with a long stem which extends posteriorly.

Figure 6B:
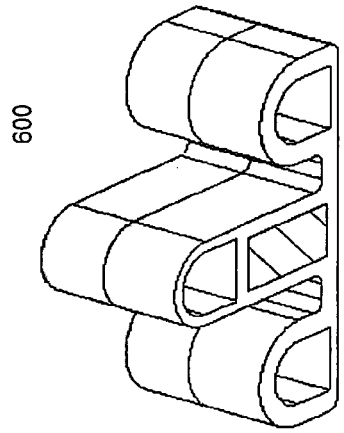
FIGS. 6A through 6G illustrate different views of the zero-profile triangular mini-plate, its integration with BDFT screws and incorporation into the vertebral bodies.
Figure 6A:
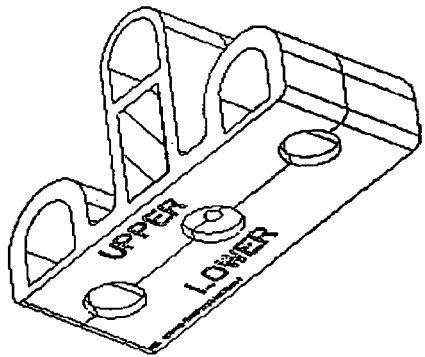
Figure 6C:
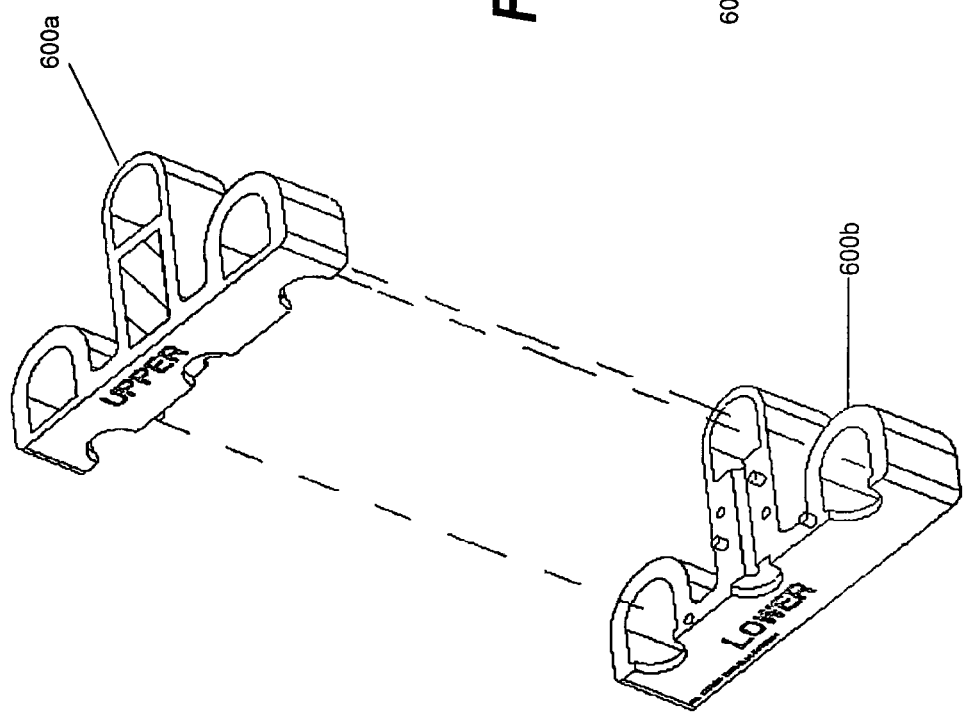
Figure 6D:
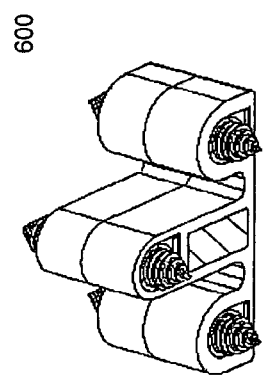
Figure 6F:
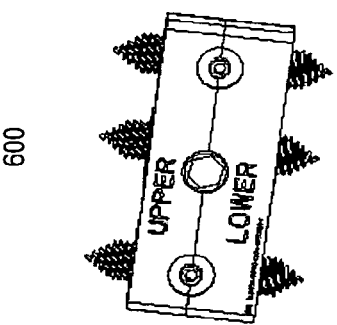
Figure 6E:
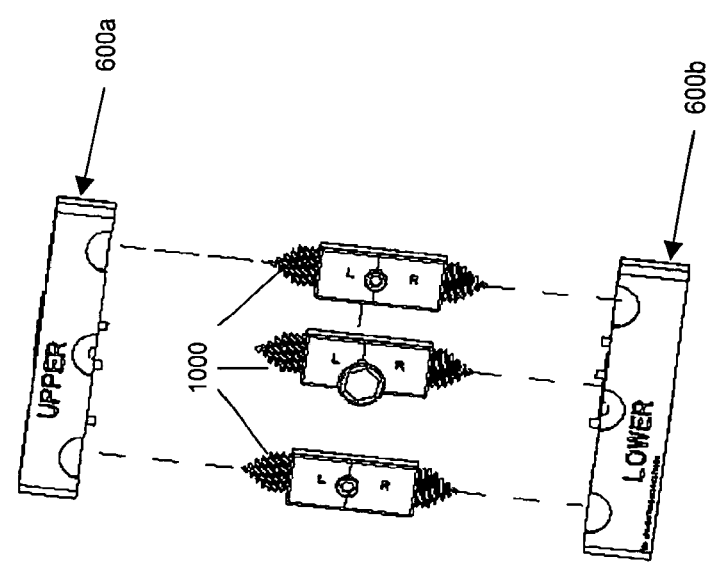
Figure 6G:
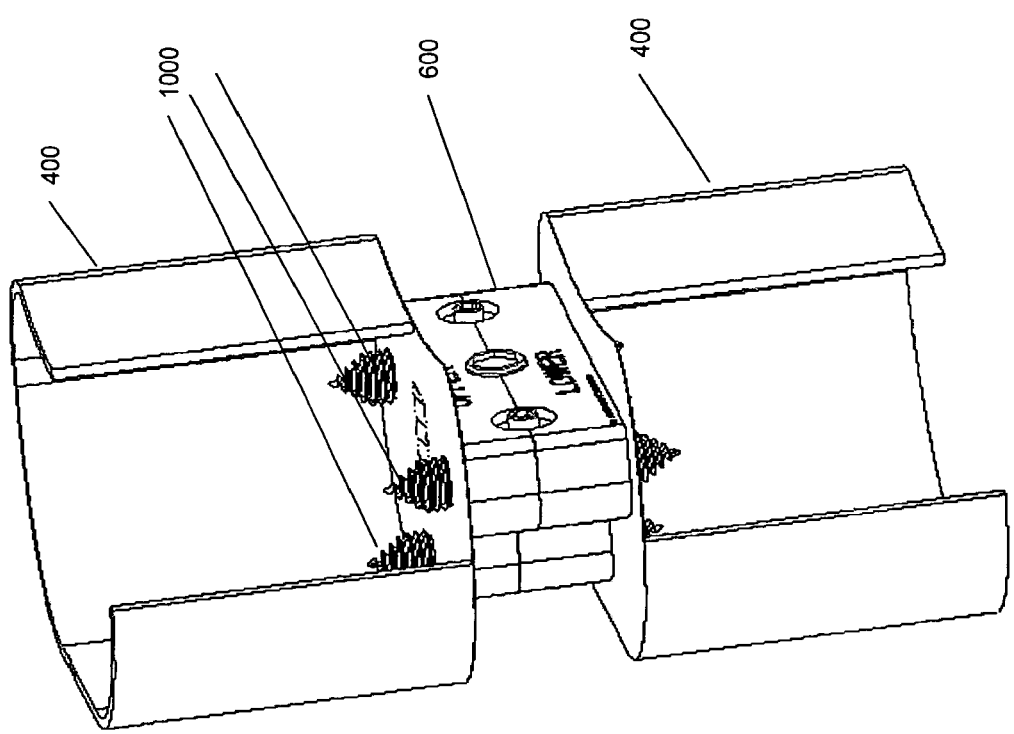
Figure 6I:
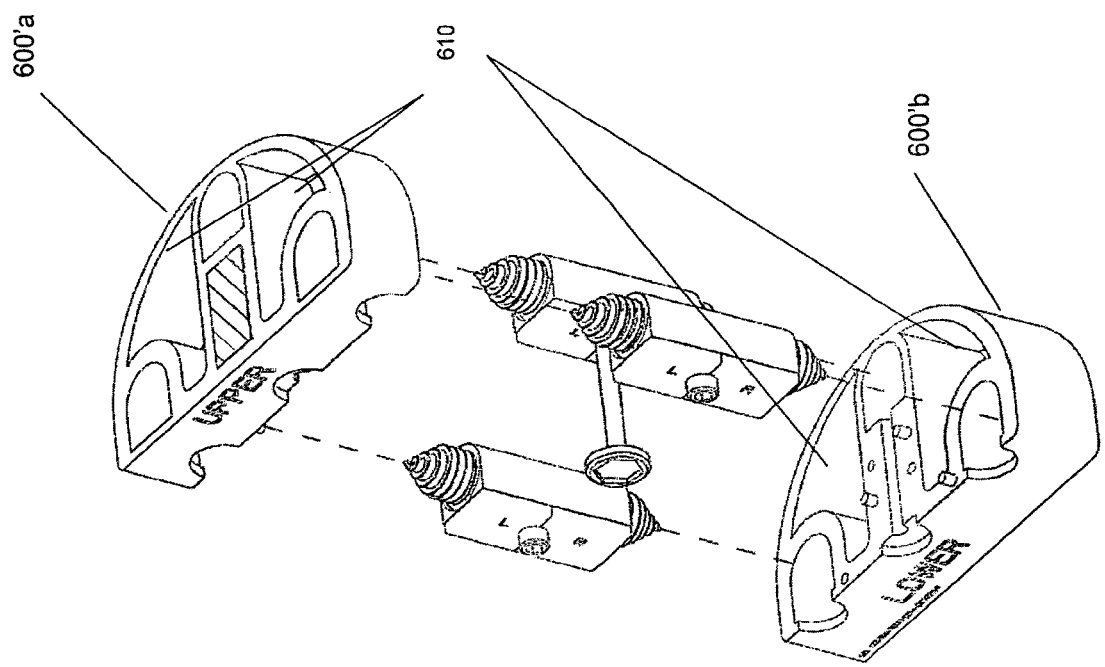
FIGS. 6H and 6I illustrate different views of the three-in-one device combining a zero-profile horizontal mini-plate, a cage with incorporated slots for the placement of bone material, and BDFT screws
Figure 6H:
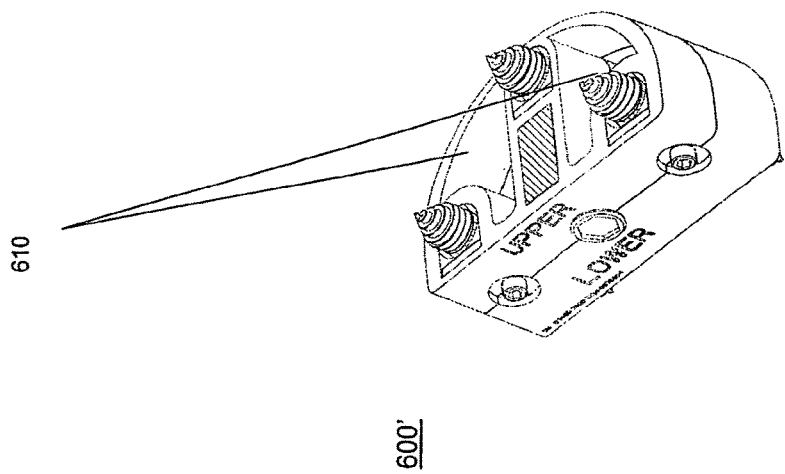

As illustrated in FIGS. 6H and 6I this embodiment 600' could be made hollow to accommodate the packing of bone material and can actually function as a combined three-in-one fusion cage/plate/BDFT screw construct. Note that this plate embodiment 600' also has upper and lower components similar to 600a, 600b (FIGS. 6A-C). Preferably, plates 600'a and 600'b, however, include slots 610 for placement of bone material. FIGS. 6D-F illustrate the incorporation of the BDFT screws 1000 into the triangular mini-plate 600. FIG. 6G illustrates the positioning of the triangular mini-plate 600 with incorporated expanded screws 1000 into adjacent vertebral bodies 400.

Figure 7A:
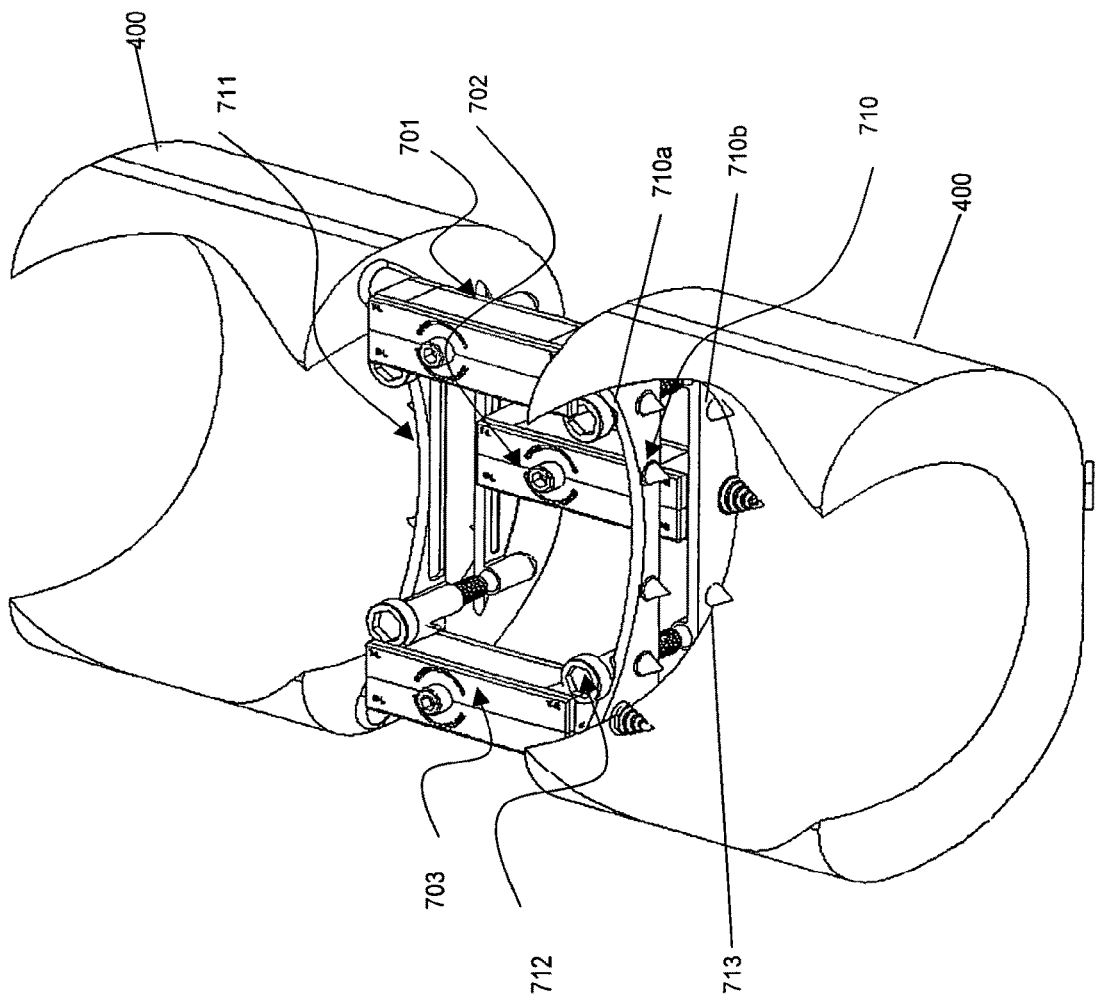
FIGS. 7A and 7B illustrate the lumbar two-dimensionally expanding intervertebral fusion device (IBFD) with incorporated BDFT screws.
Figure 7B:
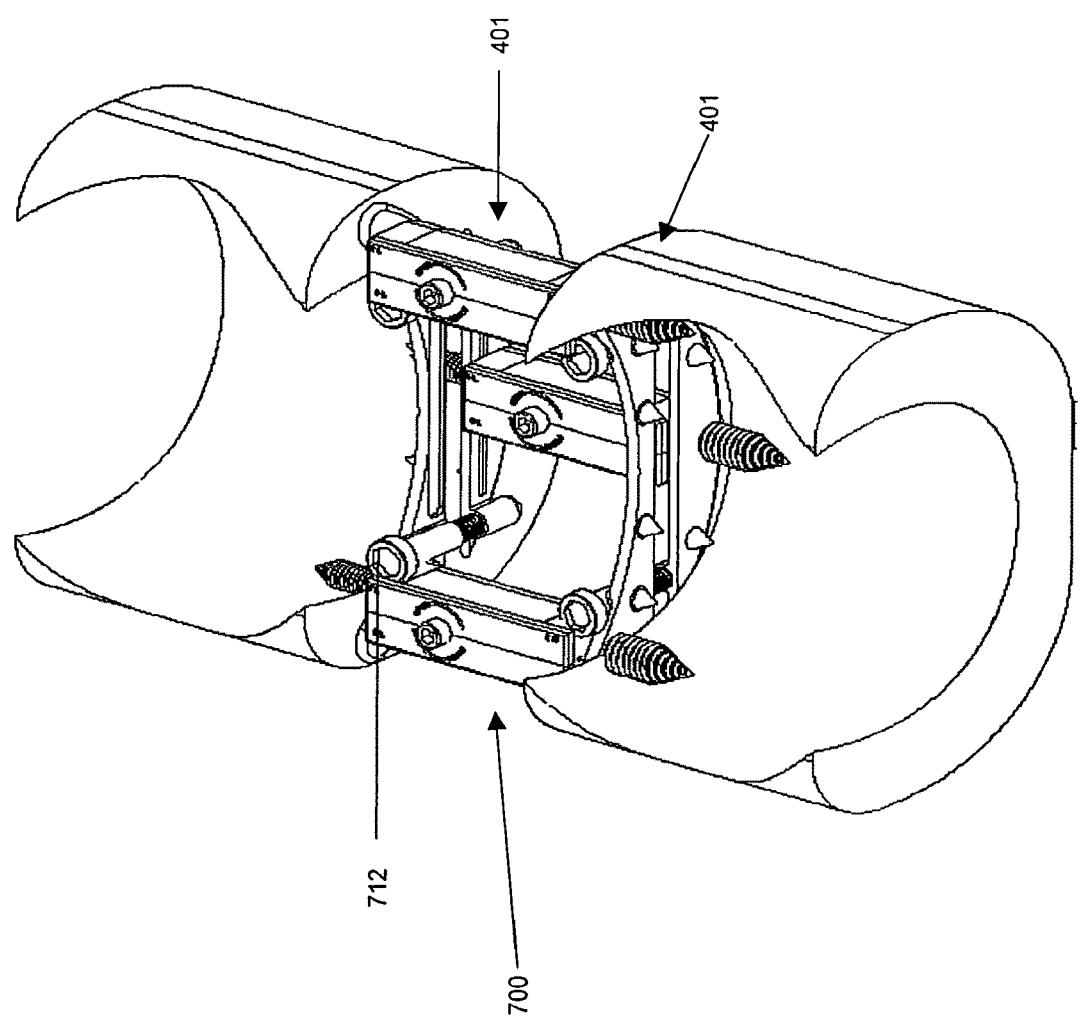

FIGS. 7A and 7B illustrate a boomerang shaped thoracolumbar IBFD 700 with ratchetable titanium or PEEK shells 710, 711 which can expand geometrically in two dimensions. FIG. 7A illustrates the BDFT screws 701, 702, 703 in partially expanded position. FIG. 7B illustrates the BDFT screws 701, 702, 703 in fully expanded position. The outer shells 710, 711 themselves when ratcheted width-wise have titanium or PEEK spikes 713 inserting themselves into and purchasing the endplates 401, thus securing permanent integration into the vertebral endplates 401. The outer shell 710, 711 surfaces can be treated with hydroxyappetite to facilitate bone incorporation. These shells are fully described in our previous PCT Patent Application PCT/US2005/016493, filed May 11, 2005.

The IBFD device 700 has four shells and a plurality of spikes 713. The height can be modified by adjusting four fixed height screws 712. Sequential turning of these screws 712 leads to height expansion between the rostra! and caudal shells 710, 711 by widening the distance between their superior and inferior shells 710a, 710b. Once the IBFD 700 is properly positioned in the interspace the spikes 713 engage and purchase the vertebral endplates 401. The three incorporated BDFT screws 701, 702, 703 are turned clockwise leading to anterior and middle column engagement of the vertebral bodies 400 above and below the disc space. The BDFT screws 701, 702, 703 are strategically placed; one on each side of the superior shell 710a and one centrally on the inferior shell 710b. This captures anterior and middle columns of the vertebral column increasing spinal stability. After the BDFT screws 701, 702, 703 are successfully purchased within the vertebral bodies 400, bone fusion substances are placed/packed or poured, into the inner aspects of the device 700 and its surrounding intervertebral space.

An alternative thoracolumbar IBFD embodiment not illustrated expands in two dimensions and has the additional feature of an incorporated expansile porous elastometric sheath molded to the inner aspects of the titanium shells. Within the balloon is a port with or without an attached microsilastic catheter through which bone fusion material can be injected. Supplemental bone fusion material can be added to the surrounding area of the device to further enhance fusion. Furthermore for certain patients where applicable, a rapid fusion can be effected by the instillation of methyl-methacrylate A similar embodiment for a cervical IBFD is based on our previously described two-dimensional cervical expansion device in PCT Patent Application PCT/US2005/016493, filed May 11, 2005.

The engagement of the IBFD shell spikes 713 and the BDFT screws 701, 702, 703 into the vertebral bodies 400 above and below the device would obviate the need for any kind of anterior plating system.

Figure 8C:
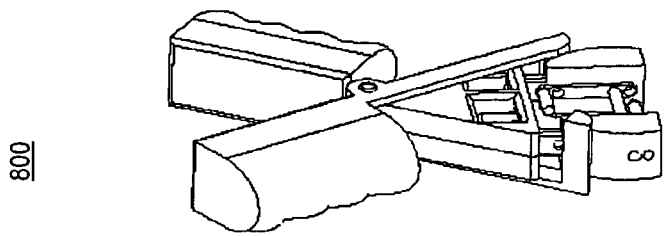
FIGS. 8A-N illustrate the facet joint calibrated stapling device which staples the inferior articulating facet with the superior articulating facet. Increasing degrees of torque calibration leads to increasing posterior column rigidity, whereas decreasing degrees of calibration leads to increasing flexibility.
FIGS. 8O and 8P illustrate four frontal and perspective views of the facet staple with sequential increasing calibrated positions leading to decreasing increments of joint motion/flexibility.
FIGS. 8Q and 8R illustrate the stapled inferior and superior interarticulating facets by the facet stapler.
Figure 8B:
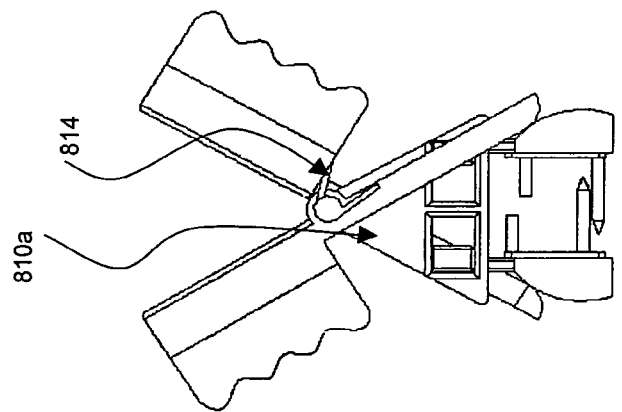
Figure 8A:
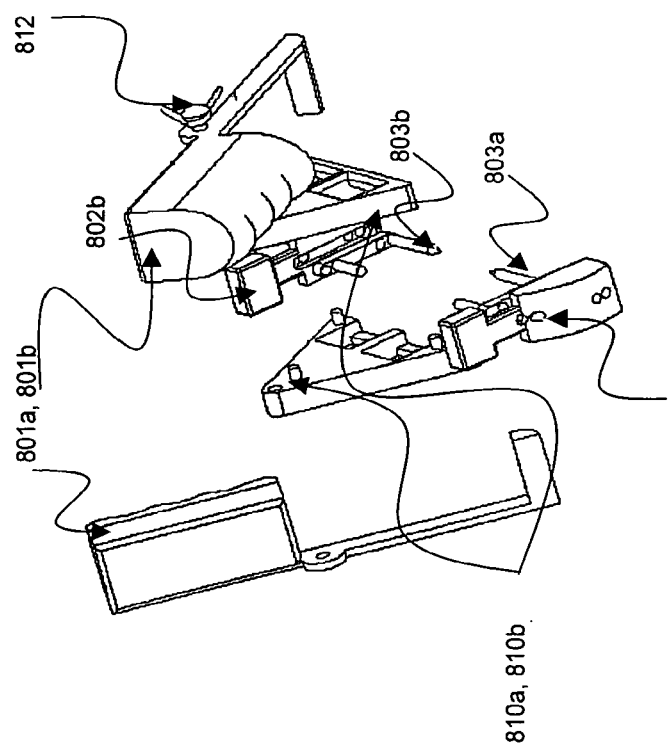

FIGS. 8A-N illustrate a calibrated facet joint stapler 800 which can be used to staple the thoracolumbar inferior and superior articulating facets with incremental torquedegrees. Incrementally increasing the degrees of calibration modulates the extent of facet joint flexibility. This can be used as an option to provide posterior column support and can be used in an open, or percutaneous, endoscopic or fluoroscopic approach. Depending on the operative approach and the individual patient, facet stapling can be performed unilaterally or bilaterally.

Figure 8E:
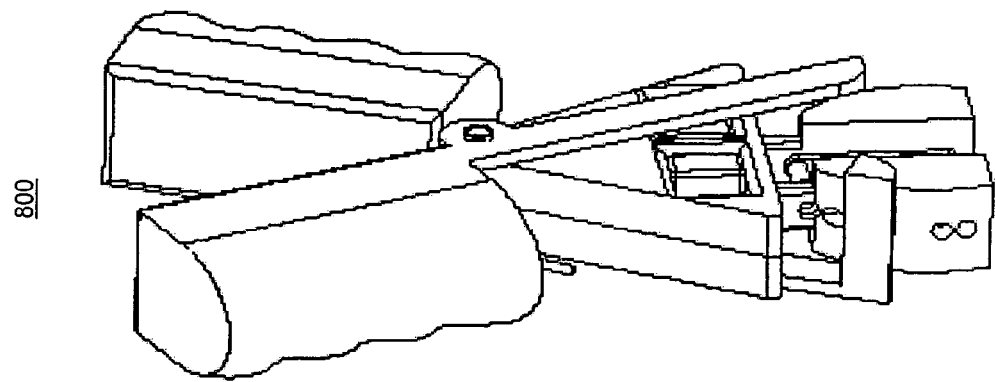
Figure 8D:
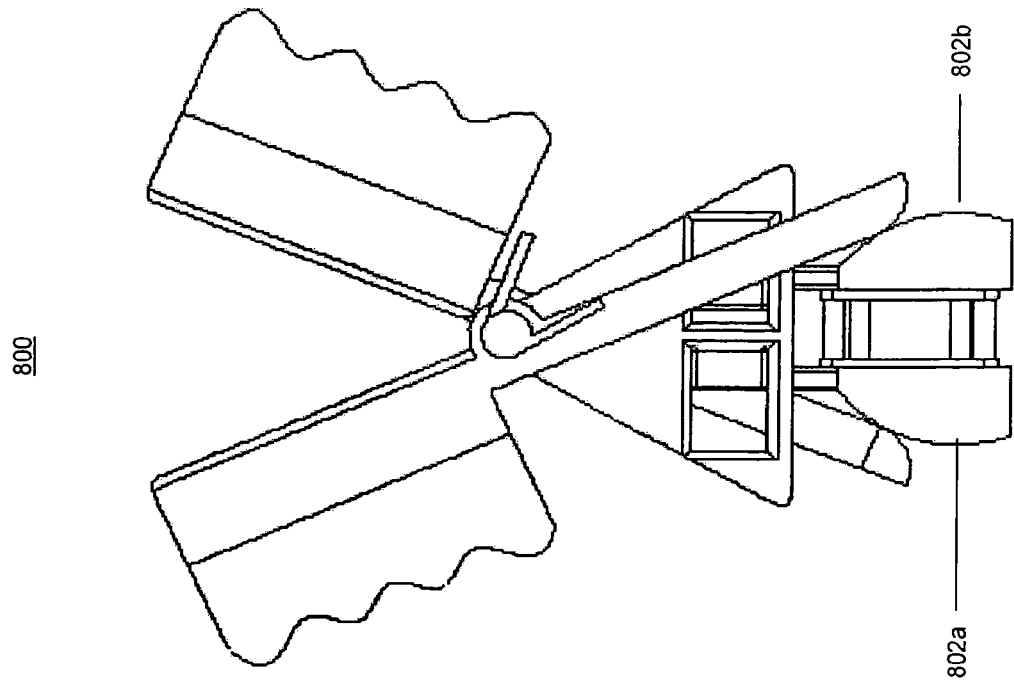

The stapling device 800 consists of two orthogonally placed levers 801a, 801b which open and close over a triangular fulcrum 810. The edges of the levers 801a, 801b are attached to left sand right staple cartridges 802a, 802b. Each cartridge 802a, 802b holds a titanium staple 803a, 803b in its slots. FIG. 8A illustrates an exploded view of the joint stapler 800 and its essential components. FIGS. 8B and 8C illustrate the stapler 800 in open position. FIGS. 8D and 8E illustrate the stapling device 800 and staples 803a, 803b in closed position. FIGS. 8F and 8G illustrate the stapling device 800 and 803a, 803b staples in closed, staple released, position. FIG. 8H-J illustrate the components of the lever 801a, 801b which includes the grip handle 815, arm 816, rounded wedge 817 and fulcrum screw hole 818. FIGS. 8K and 8L illustrate the details of the cartridge 802a, 802b including its slot for the fulcrum 810 and staples 803a, 803b. FIGS. 8M and 8N illustrate the details of the fulcrum 810 which include right and left cartridge slots 820a, 820b and fulcrum screw 812 and mating alignments. Most importantly it has four incremental calibration slots for incremental degrees of facet joint stapling. Also illustrated are spring anchors 814.

Figure 8P:
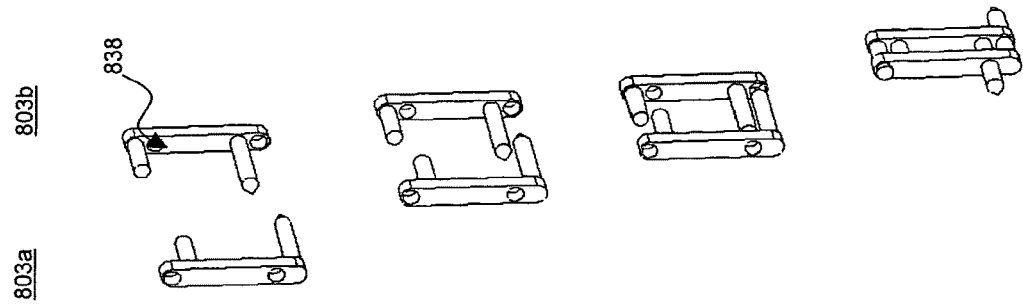
Figure 8O:
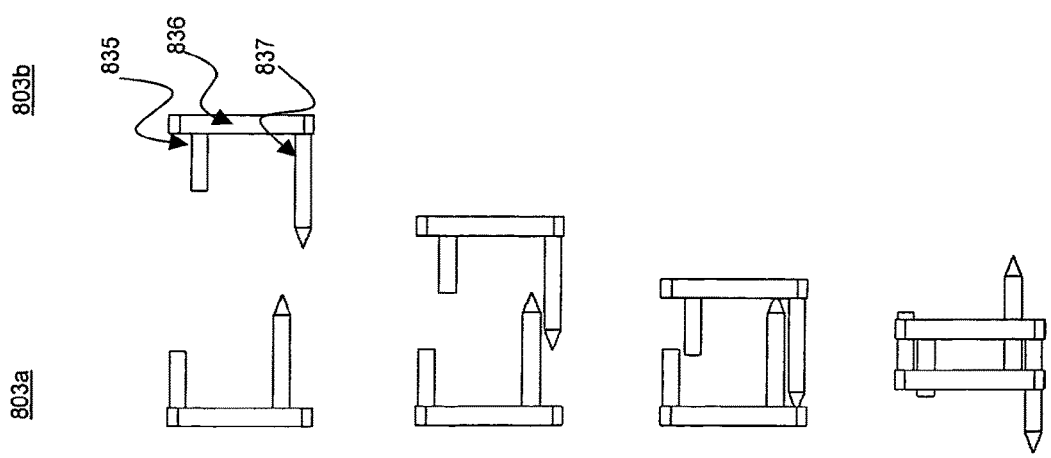

FIGS. 8O and 8P illustrate frontal and perspective views, respectively of the two opposing titanium facet staples 803a, 803b. Each staple 803a, 803b consists of a bracket 836, a nail 837 and an alignment pin 835. Illustrated are four sequential calibrated tightening positions of the opposing staples 803a, 803b. Increasing the calibrated opposition of the two staples 803a, 803b leads to increasing opposition of the facet joints and hence increasing rigidity, and decreasing flexibility. Each staple 803a, 803b has two alignment recesses 838. The opposition of these staples 803a, 803b around the facet joint forms a rectangular facet joint enclosure.

Figure 8R:
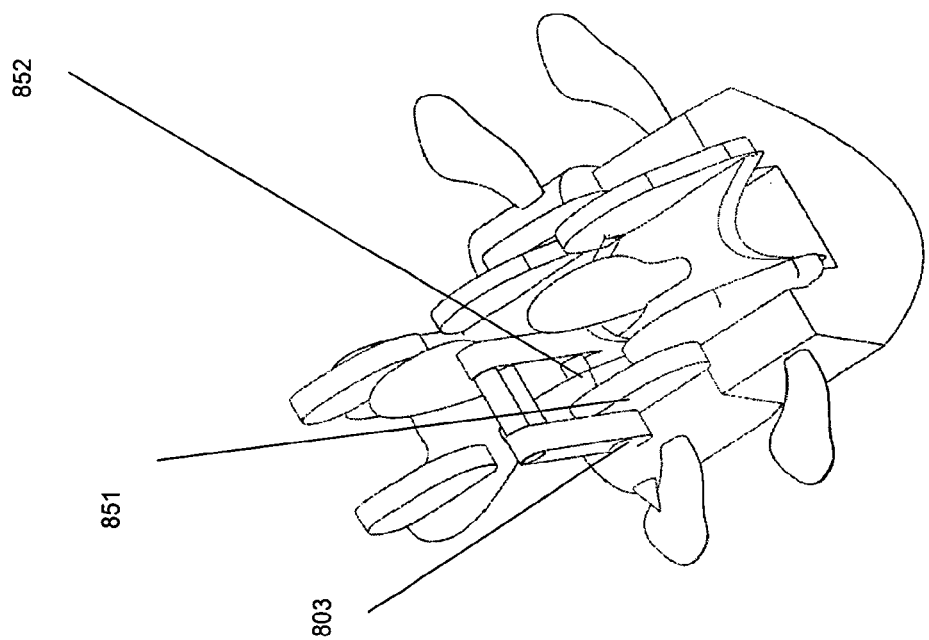
Figure 8Q:
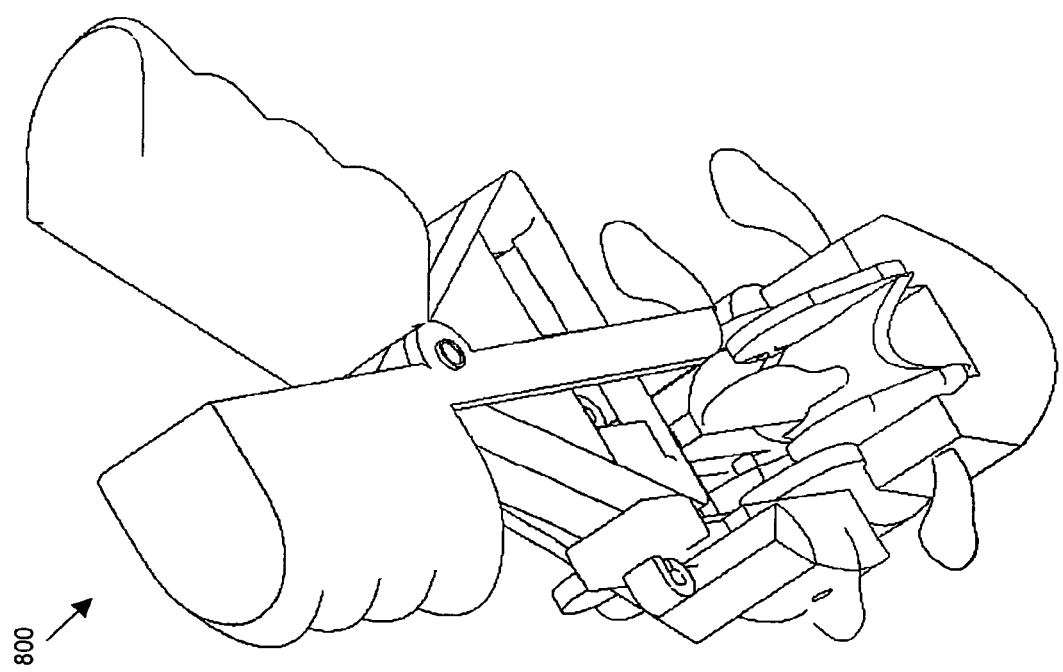

FIGS. 8Q ad 8R illustrate the stapled inferior and superior articulating facets 851, 852. FIG. 8R illustrates the application of the facet stapler 800 on the facets 851, 852 introducing the facet staple 803. The facet staple is used to join the exterior articulating facet 851 and the interior articulating facet 852.

2. The Surgical Method

The surgical steps necessary to practice the present invention will now be described.

The posterior lumbar spine implantation of the BDFT screws 1000, plate and IBFD can be implanted via a previously described posterior lumbar interbody fusion procedure (PLIF) or posterior transforaminal lumbar interbody fusion procedure (TLIF). The procedure can be performed open, microscopic, closed, tubular or endoscopic. Fluoroscopic guidance can be used with any of these procedures.

After the adequate induction of anesthesia, the patient is placed in the prone position.

A midline incision is made for a PLIF, and one or two parallel paramedian incisions or a midline incision is made for a TLIF. For the PLIF a unilateral or bilateral facet sparing hemi-laminotomy is created to introduce the BDFT screws 1000, plates or IBFD into the disc space after it is adequately prepared. For the TLIF procedure, after a unilateral dissection and drilling of the inferior articulating surface and the medial superior articulating facet, the far lateral disc space is entered and a circumferential discectomy is performed. The disc space is prepared and the endplates exposed.

There are then multiple embodiments to choose from for an intervertebral body fusion. With the first and simplest choice, under direct or endoscopic guidance one BDFT screw 1000 or three BDFT screws 1000 can be placed in a triangulating manner encompassing the anterior and middle vertebral columns (FIGS. 4A-C). The screws 1000 are then maximally expanded purchasing and uniting the vertebral bodies above and below the disc space. Bone material or an alternative intervertebral fusion device can then be packed into the disc space. The casing of the screws 1000 prevents subsidence of the vertebral bodies. An additional option in the posterior lumbar spine is to place a mini-plate dorsally underneath the thecal sac to prevent bone migration into the nerves. In addition via a TLIF approach a triangular mini-plate/cage construct can be inserted, and then the BDFT screws 1000 maximally expanded. This is a very simple and practical supplemental or stand-alone intervertebral fusion device.

Using an alternative IBFD option, utilizing specialized forceps the two-dimensional expanding thoracolumbar expandable IBFD 700 (FIGS. 7A and 7B) is introduced into the disc space. The final dimension expansion in all embodiments leads to purchasing of the spikes into the vertebral endplates. The BDFT screws 1000 are then driven directly into rostral and caudal vertebral bodies across the intervertebral space. Then bone fusion material; autologous, allograft, bone matrix protein, BMP, rh-BMP, paste or other similar currently available or specially designed osteoconductive substances can be placed into the device and the surrounding intervertebral space. In embodiments with an incorporated viscoelastic balloon sheath, prior to engaging the screws the expandable elastometric sheath/balloon is filled with bone fusion material as mentioned above. If desirable, further material, can be placed outside its confines within the intervertebral space.

If further posterior column stability or rigidity is required, unilateral or bilateral, single level or multiple level facet screw stapling can be performed under open, microscopic fluoroscopic or endoscopic vision. Radiographic confirmation of staple position is obtained. Calibrated stapling leads to opposition of the facet joints with incremental degrees of joint opposition. This can lead to variable degrees of posterior column rigidity and/or flexibility.

The anterior lumbar spine implantation of solitary BDFT screw(s) 1000, BDFT screws incorporated into a horizontal linear or triangular mini-plate, or the IBFD/BDFT screw embodiment for L4/5 and L5/S1 interspaces can be performed on the supine anesthetized patient via previously described open micropscopic or endoscopic techniques. Once the disc space is exposed and discectomy and space preparation is performed, placement of one, two or three BDFT screws 1000 with or without a ventral mini-plate, or placement of two dimensionally expanding IBFD with or without expansile elastometric sheaths and their incorporation is identical to that performed for the posterior approach.

The posterior placement of the BDFT screws 1000 alone or combined with mini-plates or with IBFD embodiments into the thoracic spine can be performed via previously described transpedicular approaches; open or endoscopic. The anterior placement of the IBFD 700 into the thoracic spine can be accomplished via a trans-thoracic approach. Once disc space exposure is obtained via either approach, all of the above mentioned embodiments can be inserted. Engagement of the devices is identical to what was mentioned above.

For anterior placement of the cervical embodiments of the BDFT screw(s) 1000 with or without the horizontal linear or triangular cervical mini-plate, and the IBFD embodiments the anterior spine is exposed in the anesthetized patient as previously described for anterior cervical discectomies. Once the disc space is identified, discectomy is performed and the disc space prepared. Implantation and engagement of all devices is identical to that described for the anterior lumbar and thoracic spines.

The present invention may provide an effective and safe technique that overcomes the problems associated with current tanspedicular-based thoracic and lumbar fusion technology, and with current vertical cervical plating technology, and for many degenerative stable and unstable spine diseases, and could replace many pedicle screw-based and anterior vertical-plate based instrumentation in many but not all degenerative spinal conditions. Calibrated facet joint screw staples can facilitate flexible fusions and could replace current static trans-facet screws.

To our knowledge there has not been any other previously described bidirectional screw for use in the spine, other joints, or for any commercial or carpentry application. The bi-directional screw 1000 described herein may indeed have applications in general commercial, industrial and carpentry industries. To our knowledge the description of zero to subzero profile anterior or posterior horizontal spinal plates which traverse the diameter of the disc space has not been previously described. To our knowledge an intervertebral three-inone construct combining bone cage, plate and screws has not been previously reported. To our knowledge calibrated facet joint staples 803a, 803b have not been previously described.

We claim:

1. An artificial intervertebral implant comprising:
   a fusion cage comprising a top wall, a bottom wall, a first sidewall, and a second sidewall, wherein portions of the top wall, the bottom wall, the first sidewall, and the second sidewall together define a first vertebral body facing surface and a second vertebral body facing surface opposite of the first vertebral body facing surface, wherein the top wall comprises a top surface extending from the first sidewall to the second sidewall, wherein the top surface is a substantially flat surface between the first and second sidewalls and between the first and second vertebral body facing surfaces, wherein each of the bottom wall and the first and second sidewalls are at least partially curved where the bottom wall connects to the first and second sidewalls when viewed from a direction facing the first vertebral body facing surface such that the top wall, the bottom wall, the first sidewall and the second sidewall together substantially form a D-shape when viewed from a direction facing the first vertebral body facing surface with the top wall forming a straight portion of the D-shape and the bottom wall and the first and second sidewalls together forming a curved portion of the D-shape, wherein the fusion cage defines at least one bone material slot extending from the first vertebral body facing surface through the fusion cage to the second vertebral body facing surface, wherein the at least one bone material slot is bounded between the top wall and the bottom wall;

a first anchor having a first anchor body and a first tapered tip, wherein the first anchor body has a first plurality of outwardly-extending bone engagement ridges, wherein the first anchor body is curved along the first anchor body, wherein the first anchor is extendable from the fusion cage to a first anchored position with the first tapered tip and the first plurality of outwardly-extending bone engagement ridges extending out of the fusion cage past the first vertebral body facing surface; and a second anchor having a second anchor body and a second tapered tip, wherein the second anchor body has a second plurality of outwardly-extending bone engagement ridges, wherein the second anchor body is curved along the second anchor body, wherein the second anchor is extendable from the fusion cage to a second anchored position with the second tapered tip and the second plurality of outwardly-extending bone engagement ridges extending out of the fusion cage past the second vertebral body facing surface, wherein the first and second anchors are configured to be sequentially extended out of the fusion cage in opposite directions such that the first anchor can be extended from the fusion cage past the first vertebral body facing surface prior to extending the second anchor out of the fusion cage past the second vertebral body facing surface and wherein the first and second anchors are substantially aligned with one another when extended such that the first tapered tip of the first anchor is positioned at a first location that is opposite of and aligned with a second location of the second tapered tip of the second anchor, wherein the top wall defines tool engagement holes that extend through the top surface of the top wall and are configured to facilitate operable engagement between at least one tool that extends along an axis that is substantially perpendicular to the top wall of the fusion cage with the first and second anchors to sequentially advance each of the first and second anchors out of the fusion cage through aligned and opposing openings defined by the first and second vertebral body facing surfaces such that the first tapered tip of the first anchor is positioned opposite of and aligned with the second tapered tip of the second anchor.

2. The artificial intervertebral implant of claim 1, wherein the first anchor is a first screw, wherein the first plurality of outwardly-extending bone engagement ridges are screw threads, and wherein the first anchor body is a screw body with a curved screw surface.

3. The artificial intervertebral implant of claim 1, wherein the first anchor rotates in a direction that is opposite to that of the second anchor when extended to the first and second anchored positions.

4. The artificial intervertebral implant of claim 1, wherein the first and second anchors comprise titanium.

5. The artificial intervertebral implant of claim 1, and further comprising an expansion mechanism operably connected to the first and second anchors, wherein the expansion mechanism comprises a tool engaging head, a rotatable shaft, a gear, and a pinion.

6. The artificial intervertebral implant of claim 1, and further comprising means for maintaining alignment of the first and second anchors.

7. The artificial intervertebral implant of claim 1, wherein at least one of the tool engagement holes is cylindrical and extends in a direction that is substantially normal to the top wall.

8. The artificial intervertebral implant of claim 1, wherein the fusion cage comprises a first cage portion forming the first vertebral body facing surface and a second cage portion forming the second vertebral body facing surface, wherein the first and second cage portions comprise titanium.

9. The artificial intervertebral implant of claim 8, wherein the first and second cage portions comprise titanium shells.

10. The artificial intervertebral implant of claim 1, and further comprising bone material configured to be packed in the at least one bone material slot.

11. An artificial intervertebral implant comprising:

a fusion cage comprising a top wall, a bottom wall, a first sidewall, and a second sidewall, wherein portions of the top wall, the bottom wall, the first sidewall, and the second sidewall together define a first vertebral body facing surface and a second vertebral body facing surface opposite of the first vertebral body facing surface, wherein the top wall comprises a top surface extending from the first sidewall to the second sidewall, wherein at least a portion of the top surface is a substantially flat surface, wherein each of the bottom wall and the first and second sidewalls are at least partially curved, wherein the fusion cage defines first and second bone material slots extending from the first vertebral body facing surface through the fusion cage to the second vertebral body facing surface, wherein the first bone material slot is bounded between the top wall, the bottom wall, the first sidewall, and a central divider, and wherein the second bone material slot is bounded between the top wall, the bottom wall, the second sidewall, and the central divider;

a first anchor having a first anchor body and a first tapered tip, wherein the first anchor body has a first plurality of outwardly-extending bone engagement ridges, wherein the first anchor body is curved along the first anchor body, wherein the first anchor is extendable from the fusion cage to a first anchored position with the first tapered tip and the first plurality of outwardly-extending bone engagement ridges extending out of the fusion cage past the first vertebral body facing surface; and a second anchor having a second anchor body and a second tapered tip, wherein the second anchor body has a second plurality of outwardly-extending bone engagement ridges, wherein the second anchor body is curved along the second anchor body, wherein the second anchor is extendable from the fusion cage to a second anchored position with the second tapered tip and the second plurality of outwardly-extending bone engagement ridges extending out of the fusion cage past the second vertebral body facing surface, wherein the first and second anchors are configured to be sequentially extended out of the fusion cage in opposite directions such that the first anchor can be extended from the fusion cage past the first vertebral body facing surface prior to extending the second anchor out of the fusion cage past the second vertebral body facing surface and wherein the first and second anchors are substantially aligned with one another when extended such that the first tapered tip of the first anchor is positioned at a first location that is opposite of and aligned with a second location of the second tapered tip of the second anchor, wherein the top wall defines tool engagement holes that extend through the top surface of the top wall and are configured to facilitate operable engagement between at least one tool that extends along an axis that is substantially perpendicular to the top wall of the fusion cage with the first and second anchors to sequentially advance each of the first and second anchors out of the fusion cage through aligned and opposing openings defined by the first and second vertebral body facing surfaces such that the first tapered tip of the first anchor is positioned opposite of and aligned with the second tapered tip of the second anchor.

12. The artificial intervertebral implant of claim 11, wherein the first anchor is a first screw, wherein the first plurality of outwardly-extending bone engagement ridges are screw threads, and wherein the first anchor body is a screw body with a curved screw surface.

13. The artificial intervertebral implant of claim 11, wherein the first anchor rotates in a direction that is opposite to that of the second anchor when extended to the first and second anchored positions.

14. The artificial intervertebral implant of claim 11, wherein the first and second anchors comprise titanium.

15. The artificial intervertebral implant of claim 11, and further comprising an expansion mechanism operably connected to the first and second anchors, wherein the expansion mechanism comprises a tool engaging head, a rotatable shaft, a gear, and a pinion.

16. The artificial intervertebral implant of claim 11, and further comprising means for maintaining alignment of the first and second anchors.

17. The artificial intervertebral implant of claim 11, wherein at least one of the tool engagement holes is cylindrical and extends in a direction that is substantially normal to the top wall.

18. The artificial intervertebral implant of claim 11, wherein at least some of the first plurality of outwardly-extending bone engagement ridges are patterned in series along the first anchor body and wherein at least some of the second plurality of outwardly-extending bone engagement ridges are patterned in series along the second anchor body.

19. The artificial intervertebral implant of claim 11, wherein at least some of the first plurality of outwardly-extending bone engagement ridges are positioned on the first tapered tip and wherein at least some of the second plurality of outwardly-extending bone engagement ridges are positioned on the second tapered tip.

20. The artificial intervertebral implant of claim 11, and further comprising bone material configured to be packed in the first and second bone material slots.

21. An artificial intervertebral implant comprising:
a fusion cage comprising a top wall, a bottom wall opposite the top wall, a first sidewall, and a second sidewall opposite the first sidewall, wherein portions of the top wall, the bottom wall, the first sidewall, and the second sidewall together provide a periphery to a first vertebral body facing surface and a periphery to a second vertebral body facing surface opposite of the first vertebral body facing surface, wherein the top wall comprises a top surface and extends from the first sidewall to the second sidewall, wherein the fusion cage defines a bone material slot extending through the fusion cage from the first vertebral body facing surface to the second vertebral body facing surface, the bone material slot being bounded between the first vertebral body facing surface and the second vertebral body facing surface; and a first anchor having a first anchor body and a first tapered tip, wherein the first anchor body has a first plurality of outwardly-extending bone engagement ridges, wherein the first anchor is extendable through the fusion cage to a first anchored position in which the first tapered tip and the first plurality of outwardly-extending bone engagement ridges extend out of the fusion cage past the first vertebral body facing surface, wherein the top wall defines a tool engagement hole that extends through the top surface and is configured to facilitate operable engagement between a tool that extends along an axis that is substantially perpendicular to the top wall of the fusion cage and the first anchor, to advance the first anchor through the first vertebral body facing surface as the tool operably engages with the tool engagement hole.

22. The artificial intervertebral implant of claim 21, comprising a second anchor having a second anchor body and a second tapered tip, wherein the second anchor body has a second plurality of outwardly-extending bone engagement ridges, wherein the second anchor is extendable through the fusion cage to a second anchored position in which the second tapered tip and the second plurality of outwardly-extending bone engagement ridges extend out of the fusion cage past the second vertebral body facing surface, wherein the tool engagement hole is configured to facilitate operable engagement between the tool and the second anchor, to advance the second anchor through the second vertebral body facing surface as the tool operably engages with the tool engagement hole.

23. The artificial intervertebral implant of claim 22, wherein:
the fusion cage defines a first slot to engage the first anchor and guide the first anchor as the first anchor extends out of the fusion cage through the first vertebral body facing surface; and
the fusion cage defines a second slot to engage the second anchor and guide the second anchor as the second anchor extends out of the fusion cage through the second vertebral body facing surface.

24. The artificial intervertebral implant of claim 23, wherein:
the first slot comprises (i) two first parallel walls that are parallel to each other and adapted to contact two first opposite sides of the first anchor, and (ii) a first perpendicular wall that extends between the two first parallel walls, is perpendicular to each of the two first parallel walls, and is adapted to contact a side of the first anchor that extends between the two first opposite sides of the first anchor; and
the second slot comprises (i) two second parallel walls that are parallel to each other and adapted to contact second two second opposite sides of the second anchor, and (ii) a second perpendicular wall that extends between the two second parallel walls, is perpendicular to each of the two second parallel walls, and is adapted to contact a side of the second anchor that extends between the two second opposite sides of the second anchor.

25. The artificial intervertebral implant of claim 23, wherein the first slot and the second slot of the fusion cage are configured to position the first anchor and the second anchor so that the first tapered tip of the first anchor is positioned at a first location that is opposite of and aligned with a second location of the second tapered tip of the second anchor, when the first anchor is extended through the first vertebral body facing surface and the second anchor is extended through the second vertebral body facing surface.

26. The artificial intervertebral implant of claim 21, wherein:
the fusion cage defines a slot to engage the first anchor and guide the first anchor as the first anchor extends out of the fusion cage through the first vertebral body facing surface; and
the slot comprises (i) two parallel walls that are parallel to each other and are adapted to contact opposite sides of the first anchor, and (ii) a perpendicular wall that extends between the two parallel walls, is perpendicular to each of the two parallel walls, and is adapted to contact a side of the first anchor that extends between the opposite sides of the first anchor.

27. The artificial intervertebral implant of claim 21, wherein the bone material slot is bounded between the first vertebral body facing surface and the second vertebral body facing surface such that an unbroken interior circumferential surface located at a center of the bone material slot between the first vertebral body facing surface and the second vertebral body facing surface surrounds the bone material slot.

28. The artificial intervertebral implant of claim 27, wherein the fusion cage defines a second bone material slot extending through the fusion cage from the first vertebral body facing surface to the second vertebral body facing surface, the second bone material slot being bounded between the first vertebral body facing surface and the second vertebral body facing surface such that a second unbroken interior circumferential surface located at a center of the second bone material slot between the first vertebral body facing surface and the second vertebral body facing surface surrounds the second bone material slot.

29. The artificial intervertebral implant of claim 21, wherein the bone material slot is bounded between the first vertebral body facing surface and the second vertebral body facing surface such that:
a first interior lateral surface proximate the first sidewall is continuous and unbroken between the first vertebral body facing surface and the second vertebral body facing surface; and
a second interior lateral slot surface proximate the second sidewall is continuous and unbroken between the first vertebral body facing surface and the second vertebral body facing surface.

30. The artificial intervertebral implant of claim 21, wherein:
the bottom wall extends from the first sidewall to the second sidewall;
the first sidewall is continuous and unbroken between the top wall, the bottom wall, the first vertebral body facing surface, and the second vertebral body facing surface; and
the second sidewall is continuous and unbroken between the top wall, the bottom wall, the first vertebral body facing surface, and the second vertebral body facing surface.

31. The artificial intervertebral implant of claim 21, wherein the first anchor defines a channel that extends from (i) a channel opening that opens to an exterior of the first anchor, to (ii) a channel end, the channel end being offset from a longitudinal axis of the first anchor and positioned between the longitudinal axis of the first anchor and an exterior surface of the first anchor, the channel end being located closer to the first tapered tip than the channel opening is located to the first tapered tip.

32. The artificial intervertebral implant of claim 31, wherein:
the first plurality of outwardly-extending bone engagement ridges includes three ridges on a first side of the first anchor and three ridges on a second side of the first anchor that is opposite from the first side of the first anchor; and
a length of the channel from the channel opening to the channel end is greater than a length between a tip of a first ridge on the first side of the first anchor and a tip of a third ridge on the first side of the first anchor, the first ridge being separated from the third ridge by a second ridge on the first side of the first anchor.

33. The artificial intervertebral implant of claim 21, wherein:
the first plurality of outwardly-extending bone engagement ridges includes five ridges on a first side of the first anchor and five ridges on a second side of the first anchor that is opposite from the first side of the first anchor.

34. The artificial intervertebral implant of claim 33, wherein:
multiple of the five ridges on the first side of the anchor have a same length measured from ridge valley to ridge tip; and
multiple of the five ridges on the second side of the anchor have a same length measured from ridge valley to ridge tip.

35. The artificial intervertebral implant of claim 21, wherein:
the top wall defines a second hole that extends through the top surface and that is offset from the tool engagement hole; and
the second hole is circular.

36. The artificial intervertebral implant of claim 35, wherein:
the top wall defines a third hole that extends through the top surface and that is offset from the tool engagement hole and the second hole;
the third hole is circular;
the tool engagement hole, the second hole, and the third hole are aligned along a central dimension of the top wall that extends from the first sidewall to the second sidewall; and
the tool-receiving hole has a different shape from the second hole and from the third hole.

37. The artificial intervertebral implant of claim 21, wherein:
the top surface is flat between the first sidewall and the second sidewall; and
exterior surfaces of the first sidewall, the bottom wall, and the second sidewall form a continuously curving surface from where the first sidewall meets the top wall to where the second sidewall meets the top wall.

38. The artificial intervertebral implant of claim 21, wherein:
the first sidewall transitions to the top wall with a first radius of curvature along an exterior of the fusion cage, the first radius of curvature being smaller than a thickness of the first sidewall proximate the top wall; and
the second sidewall transitions to the top wall with a second radius of curvature along the exterior of the fusion cage, the second radius of curvature being smaller than a thickness of the second sidewall proximate the top wall.

* * * * *

UNITED STATES PATENT AND TRADEMARK OFFICE
CERTIFICATE OF CORRECTION

PATENT NO. : 10,952,723 B2
APPLICATION NO. : 16/362152
DATED : March 23, 2021
INVENTOR(S) : Moskowitz et al.

Page 1 of 1

It is certified that error appears in the above-identified patent and that said Letters Patent is hereby corrected as shown below:

On the Title Page

Item (54) (Title), Line 1, Column 1, delete "IMPANT" and insert -- IMPLANT --, therefor.

Second Page, Column 1 item (57) (Abstract), Line 1, after "can" delete "be".

In the Specification

Column 1, Line 1, delete "IMPANT" and insert -- IMPLANT --, therefor.

In the Claims

Column 14, Line 54, Claim 24, before "two" delete "second".

Column 16, Line 23, Claim 34, before "anchor" insert -- first --.

Column 16, Line 26, Claim 34, before "anchor" insert -- first --.

Signed and Sealed this
Nineteenth Day of October, 2021

Drew Hirshfeld
*Performing the Functions and Duties of the*
*Under Secretary of Commerce for Intellectual Property and*
*Director of the United States Patent and Trademark Office*